United States Patent
Blackburn et al.

(10) Patent No.: US 11,482,325 B2
(45) Date of Patent: *Oct. 25, 2022

(54) SYSTEM FOR VERIFICATION AND MANAGEMENT OF MEDICAL OBJECTS

(71) Applicant: Scientia Potentia Est., LLC, Charleston, SC (US)

(72) Inventors: Jeremy Blackburn, Charleston, SC (US); Justin Southward, Fort Meyers, FL (US); W. Kurt Taylor, N. Charleston, SC (US); Karl David, Charleston, SC (US); Austi Critchfield, Clearwater, FL (US); Michael Lu, N. Charleston, SC (US); Tim McVicker, Charleston, SC (US)

(73) Assignee: Scientia Potentia Est., LC, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/531,746

(22) Filed: Nov. 20, 2021

(65) Prior Publication Data

US 2022/0084665 A1    Mar. 17, 2022

Related U.S. Application Data

(63) Continuation-in-part of application No. 17/531,598, filed on Nov. 19, 2021, which is a
(Continued)

(51) Int. Cl.
*G16H 40/20* (2018.01)
*G06Q 40/08* (2012.01)
*G06Q 20/38* (2012.01)

(52) U.S. Cl.
CPC .......... *G16H 40/20* (2018.01); *G06Q 20/389* (2013.01); *G06Q 40/08* (2013.01)

(58) Field of Classification Search
CPC ........ G16H 40/20; G16H 20/10; G16H 40/63; G16H 40/67; G06Q 20/389; G06Q 40/08
(Continued)

(56) References Cited

U.S. PATENT DOCUMENTS

| | | |
|---|---|---|
| 5,752,621 A | 5/1998 | Passamante |
| 6,330,957 B1 | 12/2001 | Bell-Greenstreet |

(Continued)

FOREIGN PATENT DOCUMENTS

| | | |
|---|---|---|
| EP | 1552805 | 7/2005 |
| EP | 2052678 | 4/2009 |
| WO | 2017087926 | 5/2017 |

OTHER PUBLICATIONS

Rubbermaid Healthcare, M38 RX Mobile Medication Cart, Supplemental Operating Manual, Revised Mar. 25, 2013, 13 pages, M38 Manual 9M38-RX-xxx V8.doc, publisher and country of publication unknown.
(Continued)

*Primary Examiner* — Garcia Ade
(74) *Attorney, Agent, or Firm* — Kim and Lahey Law Firm LLC; Douglas W. Kim

(57) ABSTRACT

This system if directed to verifiably pairing a medications or container with a digital representation and can include a computer system disposed at a use location and in communication with a persistent storage and a set of non-transitory computer readable instructions included in the computer system adapted for: creating a medical article record, creating a regulatory record, associating the regulatory record with the virtual representation, storing the medical article record and the associated regulatory record on the persistence storage, creating a transaction record representing a transfer of the article from a first entity to a second entity wherein the transaction record includes a transaction verification, transmitting a payment request according the trans-
(Continued)

action verification to a second entity account representing payment for the medical article from the second entity to the first entity, and, storing the medical article record and the associated significance record on the persistence storage.

30 Claims, 31 Drawing Sheets

Related U.S. Application Data continuation-in-part of application No. 17/344,043, filed on Jun. 10, 2021, which is a continuation-in-part of application No. 17/230,911, filed on Apr. 14, 2021, now Pat. No. 11,288,761, which is a continuation-in-part of application No. 17/176,056, filed on Feb. 15, 2021, now Pat. No. 11,288,308, which is a continuation-in-part of application No. 17/128,084, filed on Dec. 19, 2020, which is a continuation-in-part of application No. 16/997,840, filed on Aug. 19, 2020, which is a continuation-in-part of application No. 16/994,585, filed on Aug. 15, 2020, now Pat. No. 11,232,652, which is a continuation-in-part of application No. 16/991,916, filed on Aug. 12, 2020, now Pat. No. 11,216,823, which is a continuation-in-part of application No. 16/876,080, filed on May 17, 2020, which is a continuation-in-part of application No. 16/810,782, filed on Mar. 5, 2020, now Pat. No. 11,216,781, which is a continuation-in-part of application No. 16/510,642, filed on Jul. 12, 2019, now Pat. No. 11,216,772, and a continuation-in-part of application No. 16/510,634, filed on Jul. 12, 2019, now Pat. No. 10,713,737, which is a continuation-in-part of application No. 16/452,076, filed on Jun. 25, 2019, now abandoned.

(58) Field of Classification Search
USPC .......................................................... 705/2
See application file for complete search history.

(56) References Cited

U.S. PATENT DOCUMENTS

| | | | |
|---|---|---|---|
| 8,407,068 B2 | 3/2013 | Ohmura et al. | |
| 8,479,988 B2 | 7/2013 | Louie et al. | |
| 8,488,842 B2 | 7/2013 | Wood et al. | |
| 9,135,768 B2 | 9/2015 | Heffron | |
| 9,626,484 B2 | 4/2017 | Olson et al. | |
| 10,338,913 B2 * | 7/2019 | Franchitti | G06N 5/022 |
| 10,832,207 B2 | 11/2020 | Vahlberg et al. | |
| 2010/0264158 A1 | 10/2010 | Van Ooyen et al. | |
| 2014/0149131 A1 | 5/2014 | Bear et al. | |
| 2017/0031676 A1 * | 2/2017 | Cecchetti | G06F 21/64 |
| 2017/0235916 A1 | 8/2017 | Woodyear et al. | |
| 2018/0289590 A1 | 10/2018 | Graska et al. | |
| 2019/0042702 A1 | 2/2019 | Chandramouli et al. | |
| 2019/0279142 A1 | 9/2019 | Andrews | |
| 2020/0098460 A1 | 3/2020 | Banks et al. | |

OTHER PUBLICATIONS

RX Systems Inc, Refurbish Manual Medication Carts Version 2 & 3, manual, date unknown, 43 pages, version 2 & 3, publisher and country of publication unknown.

Touchpoint Medical, medDispense, presentation materials / brochure, Aug. 16, 2021, 40 pages Aug. 16, 2021-BR-medDispense powered by medLogic-EN, publisher and country of publication unknown.

Touchpoint Medical, Medication Management Solutions, presentation materials / brochure, Aug. 23, 2021, 48 pages Aug. 23, 2021-BR-Medication Management Solutions Catalog-EN, publisher and country of publication unknown.

Henry I. Miller, M.S., M.D. & Wayne Winegarden, Ph.D., Fraud in Your Pill Bottle The Unacceptable Cost of Counterfeit Medicines, symposium, Oct. 2020, 22 pages, Pacific Research Institute, USA.

National Institute of Drug Abuse, Misuse of Prescription Drugs Research Report, research report, Revised Jun. 2020, 29 pages, National Institute on Drug Abuse; National Institutes of Health; U.S. Department of Health and Human Services, USA.

Stephanie Webster, Tackling the challenge of counterfeit medical devices across global healthcare settings, web-based news media, Jul. 2, 2020, 5 pages, NS Medical Devices—Progressive Media International Limited, UK.

* cited by examiner

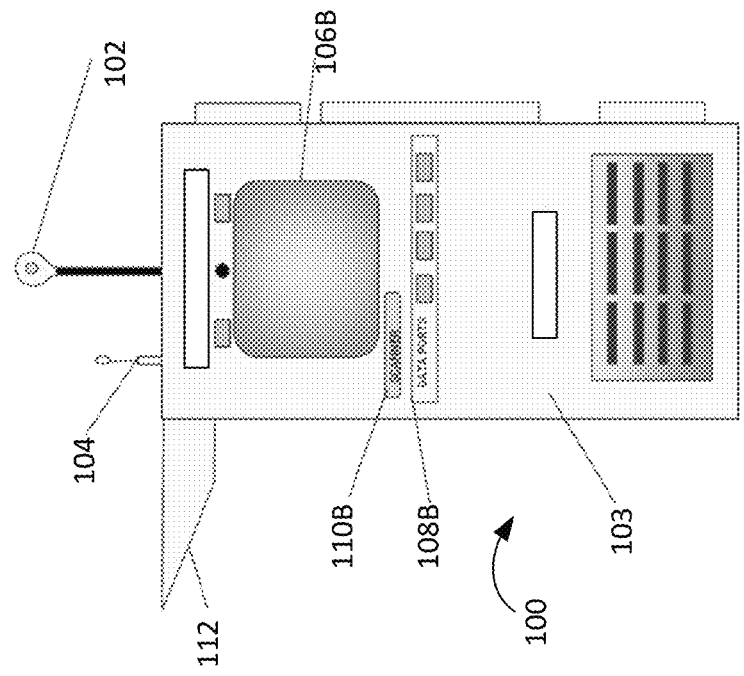
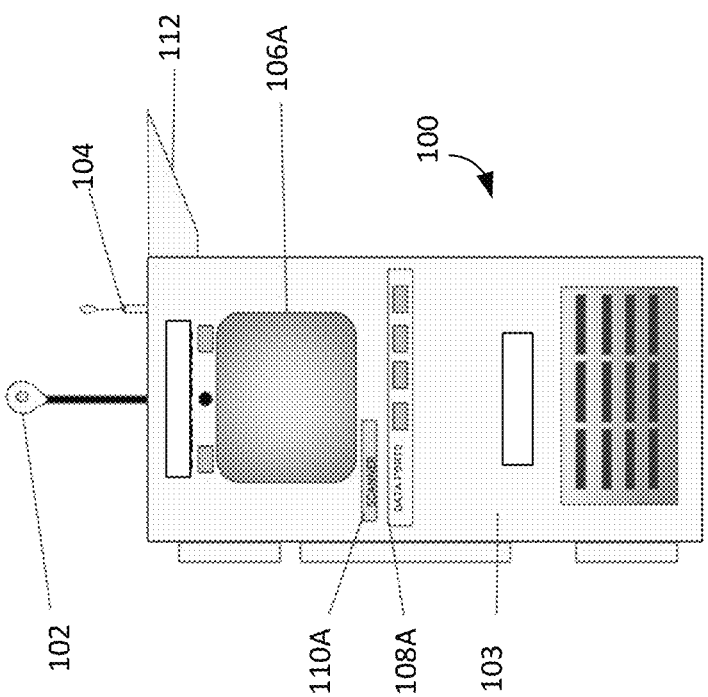

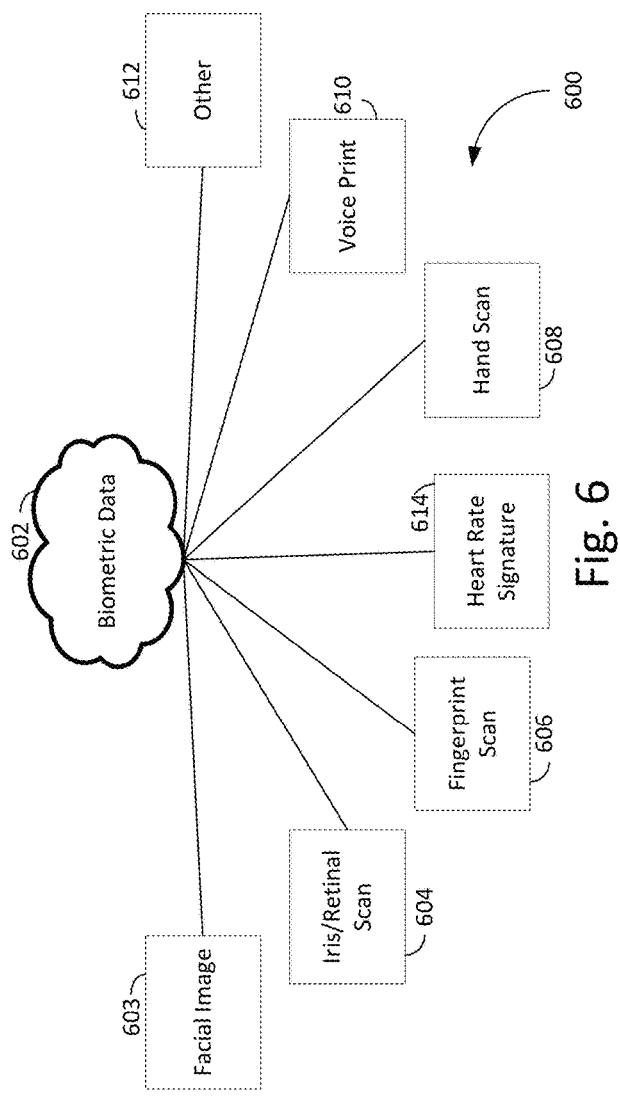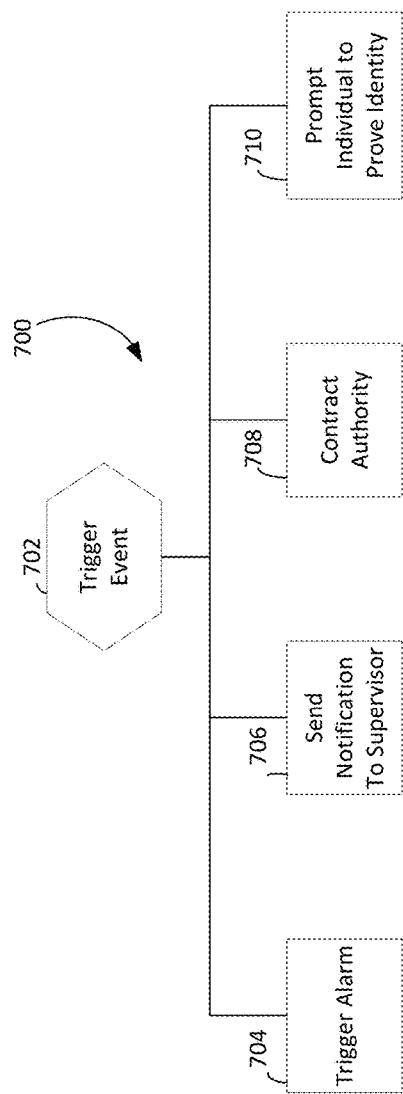

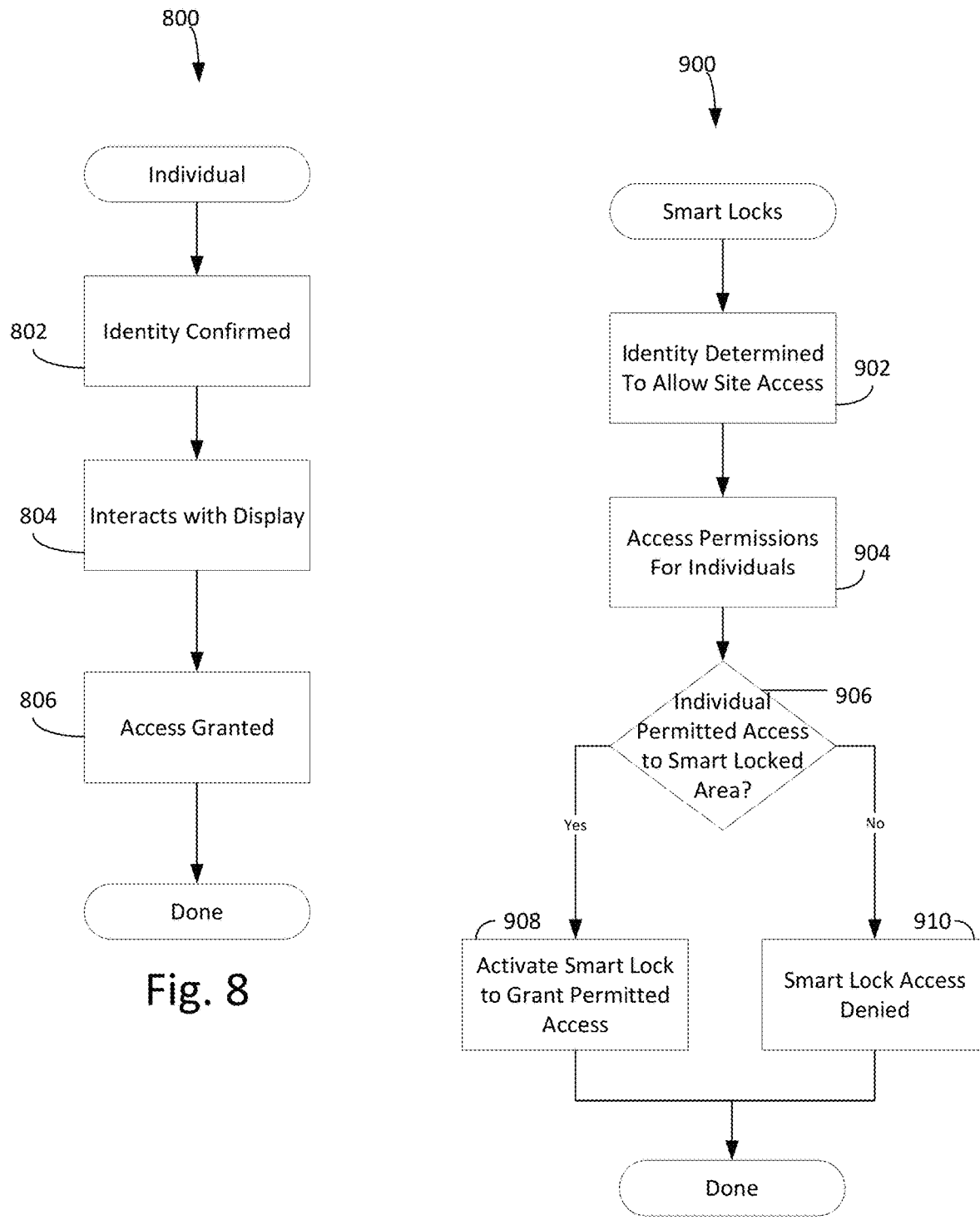

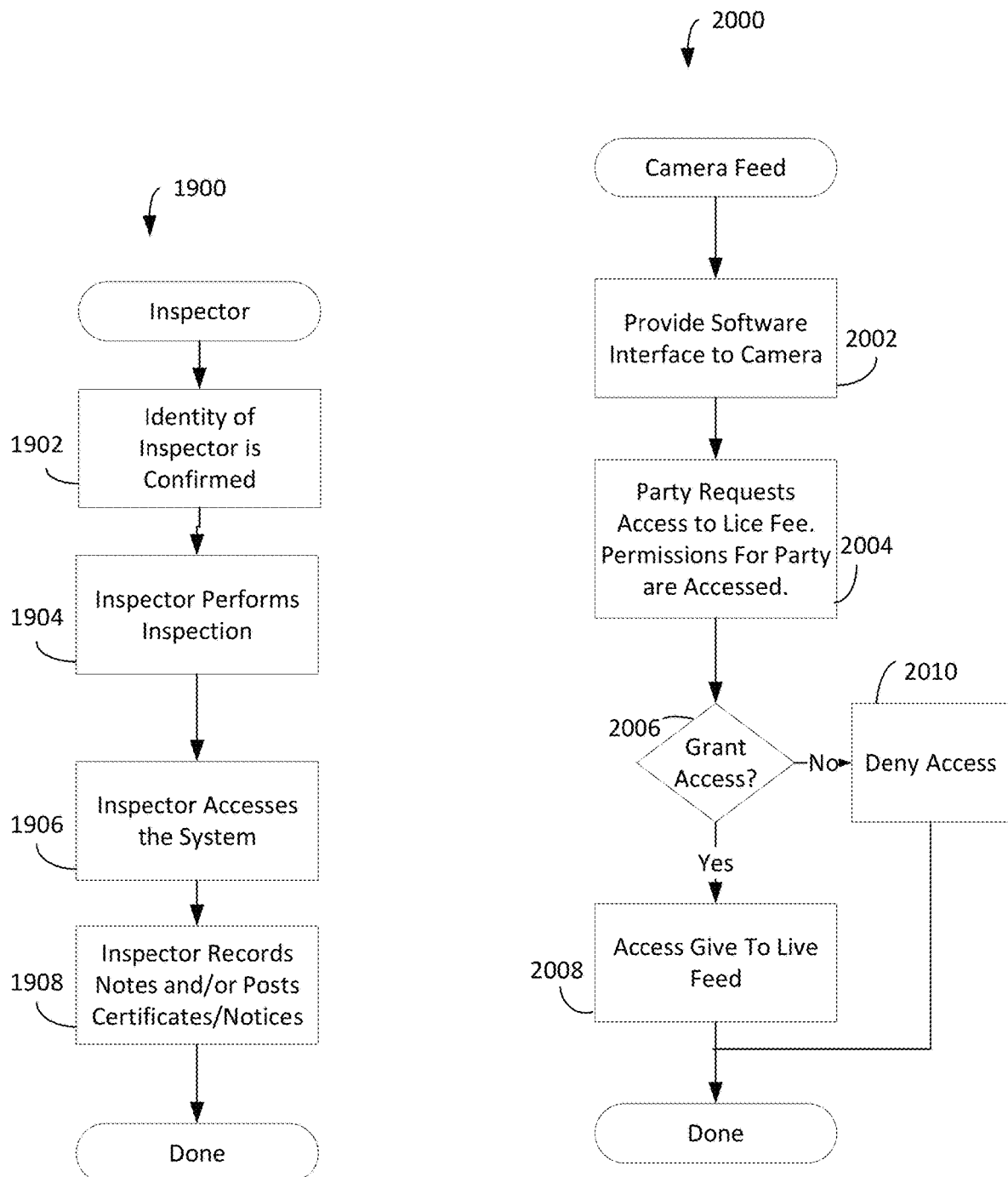

SYSTEM FOR VERIFICATION AND MANAGEMENT OF MEDICAL OBJECTS

RELATED APPLICATIONS

This application is a continuation in part of U.S. application Ser. No. 17/531,598 filed Nov. 19, 2021 which in turn is a continuation in part of U.S. application Ser. No. 17/344,043 filed Jun. 10, 2021 which in turn is a continuation in part of U.S. application Ser. No. 17/230,911 filed Apr. 14, 2021 which in turn is a continuation in part of U.S. application Ser. No. 17/176,056 filed Feb. 15, 2021 which in turn is a continuation in part of U.S. application Ser. No. 17/128,084 filed Dec. 19, 2020 which in turn is a continuation in part of U.S. application Ser. No. 16/997,840 filed Aug. 19, 2020, which is a continuation in part of U.S. application Ser. No. 16/994,585 filed Aug. 15, 2020 which in turn is a continuation in part of U.S. patent application Ser. No. 16/991,916 filed on Aug. 12, 2020 which in turn is a continuation in part of U.S. patent application Ser. No. 16/876,080 filed May 17, 2020 which in turn is a continuation in part of U.S. patent application Ser. No. 16/810,782 filed on Mar. 5, 2020 which in turn is a continuation in part of U.S. patent application Ser. No. 16/510,634 filed on Jul. 12, 2019 (now U.S. Pat. No. 10,713,737 issued Jul. 14, 2020) and U.S. patent application Ser. No. 16/510,642 filed on Jul. 12, 2019, which are all incorporated by reference. Patent Application Nos 16510542 and 16510634 are both continuations of U.S. patent application Ser. No. 16/452,076 filed Jun. 25, 2019, which all are incorporated by reference.

BACKGROUND

1) Field of the System

A system for pairing physical articles, events, and tasks such as medical research, medical treatments and evaluations, medical devices and medications and virtual representation to verify a link between the activity and article with its virtual representation to create an undichotomized pair that can be used for authentication, verification, anti-counterfeit, appraisals, auditing, recording and the like of the status, activity, and transactions associated with the medical device, task, medication, or medication container. A system for pairing medical events utilizing location data, when, biometric identity of the patient or participant, biometric identification of the provider or administer, to pair an occurring event with a digital representation that can be adapted for use with insurance, billing, or other administrative process. The verified digital data collected can be used to effectuate smart contracts to facilitate automatic payments between entities as well as to automatically detect, determine, and record compliance with requirements, private and governmental.

2) Background

There is a significant market for medical devices and medications including controlled, restricted, and prescribed medications. Concerning medications, some medications have increased risk, value, need for control and subject to more abuse. It has been reported that prescription drugs are subject to more abuse in older adults, and this has been a growing problem. It would be advantageous to have a system that better controlled the supply chains of such drugs from the manufacturer of raw materials to the patient. While there have been efforts to address this problem, these efforts are subject to many exposing issues that result in mistakes in the making, distribution, prescription, dispensing and use of drugs. According to the National Center for Biotechnology Information each year, in the United States alone, 7,000 to 9,000 people die because of medication error.

Further, counterfeit prescription drugs are a growing concern as these illegal, hazardous, fake medicines not produced to the pharmacological specifications of the drugs they claim to be. Counterfeit prescription drugs may be contaminated or contain incorrect ingredients or even no active ingredient at all. Counterfeit drugs may include the correct right active ingredient but with the wrong dosage. The Federal Bureau of Investigation states that to combat counterfeit drugs, consumers should (a) be mindful of appearance and closely examine the packaging and lot numbers of prescription drugs, (b) be alert to any changes from one prescription to the next, (c) consult your pharmacist or physician if your prescription drug looks suspicious, (d) alert your pharmacist and physician immediately if your medication causes adverse side effects or if your condition does not improve, (e) use caution when purchasing drugs on the Internet, (f) do not purchase medications from unlicensed online distributors or those who sell medications without a prescription, (g) only use reputable online pharmacies will have a seal of approval called the Verified Internet Pharmacy Practice Site (VIPPS), provided by the Association of Boards of Pharmacy in the United States and (h) be aware that product promotions or cost reductions and other "special deals" may be associated with counterfeit product promotion. While this guidance can be helpful, it is fraught with problems, mistakes, and risks.

Common counterfeits include cardiovascular medications, antibiotics, cancer drugs, ED medications, treatments for chronic ailments like HIV, diabetes & Alzheimer, painkillers and weight loss medications and psychiatric medications. Counterfeit drugs can include road paint, antifreeze, or an undeclared and unapproved medication like Sibutramine. Health risks, including death, while the most significant, are not the only negative effect of counterfeit drugs. In one report, it has been estimated that under several economic scenarios, financial loss is in the range of $17 billion to $73 billion in lost research and development, $37 billion to $162 billion in lost revenues, $4.5 billion to $19.5 billion in lost taxes and 57K to 247K jobs.

Even when drugs are not counterfeit, there is also a significant problem with prescription drug misuse. Misuse of prescription drugs means taking a medication in a manner or dose other than prescribed; taking someone else's prescription, even if for a legitimate medical complaint such as pain; or taking a medication to feel euphoria (i.e., to get high). According to one report, three classes of medication that are most misused are: (a) opioids, (b) central nervous system depressants and (c) stimulants. The ability to better control the supply chain of these drugs is a problem that needs addressing. The same report reported that in 2017, an estimated 18 million people (more than 6 percent of those aged 12 and older) have misused such medications at least once in the past year. The Substance Abuse and Mental Health Services Administration reported that the fastest-growing drug problem in the United States is prescription drugs, especially with teenagers, and exceeds cocaine, heroin, and methamphetamines.

The issues with authenticity and counterfeits are not limited to medications as it also pertains to medical devices. In 2010, the World Health Organization reported that eight percent of all medical devices in circulation are known to be fake, but actual numbers are likely to be significantly higher.

The problem is compounded with the lack of effective regulation and weak enforcement capacity, as well as the increasingly innovative strategies employed by counterfeiters. One suggested method of authentication medical devices is to add dust-sized or microparticles into the packaging, labels, or device itself. These are made of silicon dioxide and can carry digital information that can be used to identify, trace, and authenticate products. However, this suggestion fails to immutable link the markers with the actual physical object in a manner that insures authentication from creation through to the user. Further, this suggestion lacks third party verification as well as external verifications of authenticity. There have been some attempts to reduce or prevent counterfeit medical devices such as European Patent Application 2052678 that discloses holograms or electronic identifiers, in particular high-frequency labels (RFID labels), which can be adhered to medicament packaging. The problem with these techniques is that there is no assurance that the label is attached to a genuine part.

There is also a need to improve the drug trial process. The need for improved confirmation of what was given to whom, when and what conditions existed, such as the participants, patients or other subject's vitals, and what object, such as medical device, medication, treatment and the like was administered, are a necessity to prove out the efficacy as well as the audit trail related to testing and trials. There is currently not a system that tracks, immutably and autonomously, these data points as the current systems still reliant upon human input which can lead to misrepresentations, errors, and even fraud.

There is a need to improve the medical billing and administrative processes that are associated with the healthcare industry. Medicare, Medicaid, and other insurance activities are susceptible to fraud which results in unnecessary costs to insurance companies and taxpayers that can be in the hundreds of millions of dollars per year. A system that creates an immutable record of verifies the patient, participant, treatment, event, and other activity and pairs the event or treatment to a digital representation that does not rely exclusively upon trusting the digital information alone would be advantageous. The digital representation can represent medical devices, medications, treatments, locations, providers, healthcare workers, and the like so that an immutable record is provided that can reduce, if not eliminate, fraud. Verifying who, when, what, where, in an immutable database record utilizing location, block chain, or other immutable or indelible mediums, biometrics, and other data as described herein can provide for an autonomous processing of not only billing and payments but other administrative processes. Such a system could reduce the healthcare industry costs for these tasks by as much as 40% to 50% which could result in lower costs and thus resulting in lower insurance premiums. Autonomously verification and storage of digital representations would not only save money and time related to unnecessary costs and fraud but also would expedite payments resulting in better cash flows and ease of auditing.

There is also an issue with a chain of title or custody for articles such as medical devise, medicines, and medical containers. Current systems have a lack of accountability, verification and reliability of information related to the article and transactions. The inability to verify or authenticate articles and other factors can result in loss, mistakes, increased insurance claims, fraud, increased insurance premiums. Injury and death. While there have been some attempts to add item information to a physical material, such as U.S. Pat. No. 8,321,302, these attempts have focused on tracking inventory levels and do not include verifiably pairing a physical material with a virtual representation that can be tracked throughout a process. Further, these prior attempts focus on a single location and do not consider the fact that the physical location of the article can be at separate locations from creation to distribution and use. This disadvantage can be seen in U.S. Pat. No. 8,521,620 which specifically states that if a RFID tag is lost or damaged, the system allows a user to enter an item number or style and tags of similar items are displayed, a new tag is generated and associated with the item having the lost or damaged tag. Once the RFID tag is lost or damaged, the medications or container is no longer paired. While this system specifically allows for the replacement of RFID tags on the same item, it lacks the ability to verifiably pair the new tag with the medications or container.

The disadvantages of current systems are caused in part due to the lack of immutable associating the medical device, medication, or container with the virtual representation to determine that the article promised and delivered are properly physically and digitally paired. Attempts to provide for inspections (e.g., authentications) that an article is original have not solved the existing problems. There is also a need to verify that the individuals during the creation, authentication and transactions are who they say that they are, and what tasks they completed.

There is also a need to verify that the actions being performed by the individual is in compliance with applicable standards, regulations and other requirements. Specifications in some processes can include the specification of an authentication process, commercialization process of other performance criteria of the article. Specifications can include initial registration and transaction requirements and notifications.

It would be advantageous to have a system that could have medications and/or medical device specifications or requirements related to such things as patient vitals, time of administration or dosage, or licensure and/or training of the individuals involved in the event in an immutable data record where a system could compare the conditions at the time of the event to the specifications and requirements of the medication or medical device. An immutable record of the event would be useful for future diagnoses and medical evaluations of the patient or persons involved in the event as well as tracking for insurance or other purposes.

It would be advantageous to have a system that verified proper articles, authorized individuals, proper environmental and that these items and tasks are properly paired with a virtual representation. It would be advantageous to have a system that reduced or eliminates the risk of a counterfeit, fraud, substitute, lesser quality or other non-designated or approved article being used. It would be advantageous for a system that prevented or reduced the risk of counterfeit, unlicensed or unauthorized articles. It would be advantageous to have a system that allows for third party or automated independent verification to reduce counterfeit, fraudulent, false, or misleading information and activity.

The use of inspectors can assist with reducing the risk of unauthorized articles or activities. One disadvantage of an inspection is that it occurs at a point in time after an action and cannot verify proper articles, activities, and individuals. For example, in the manufacturing of medications, the raw materials, conditions, process and procedures are important else the medication can lose is efficacy and even create additional risks. Manufacturing processes should be controlled and documented so that the medication properly provides the treatment that has been designed. Further, the authentication of the materials, activities and individual should be authenticated and immutable associated with a virtual representation. The inability for a system to properly track material, activities and individuals can negatively impact research and results. For example, in 2011 a paper about sleep apnea was retracted from the New England Journal of Medicine due to the authors' inability to locate original data. Further, a survey of 90 major research institutions' research integrity officers showed that 38% of 553 misconduct cases involves some degree of poor record keeping. Further, a 2007 National Institute of Health survey found that of 1,479 researchers, 27.5% admitted to inadequate record keeping. There are even reports of expressly fraud in the testing of drugs and trials resulting in tremendous damage to both the medical industry and patients, participates and health care workers.

Further, drug manufacturers and pharmaceutical companies are often unaware or lack visibility concerning how, when, when and by whom medications drugs are administered or what procedures occur. This lack of information occurs despite the fact that pharmaceutical companies face hundreds of millions and even billions of dollars in potential liability. A system where there is transparency or visibility to the pharmaceutical companies in an immutable storage system would be of high value to the pharmaceutical companies and industry in general. Additionally, visibility or transparency for the services, treatments, medications, and medical devices that are given to patients would also provide much value to insurance companies. As previously discussed each year, Medicaid and Medicare, government insurance programs, lose billions of dollars to fraud. A system is needed whereby patients could be verified and paired to their insurance as well as paired to the actual device, medication and treatment in an immutable striate system verifying where, when, and by whom medications and treatment was given which can reduce or eliminate insurance fraud.

While inspections can improve accuracy and integrity, they do not solve the problems. U.S. Pat. No. 7,508,973 discloses a method of inspection of defects which includes assigning a plurality of sets of image acquisition conditions, executing inspection using each of the sets of conditions, classifying all detected defects into real defects and false defects by use of an automatic defect classification function, and selecting, from the plurality of sets of conditions, a set of conditions ideal for detection. However, this attempt does not allow the inspector to verify that the material used and processed complies with the design and specification using a paired virtual representation.

It would be an advantage to have a system that can pair physical articles with virtual representation so that authentication can be easily and quickly accomplished in real time.

It would be advantageous to have a system that provides for multi-party verification of the pairing of a medications or container with a virtual representation for tracking of the physical article. This tracking could happen autonomously and with location confirmation.

It would be advantageous to have a system that provides for a verified trustworthy association between physical material and virtual representations.

It would be advantageous to have a system that provides for a verified trustworthy association between physical material and virtual representations that is stored on an immutable or persistent ledger.

It would be advantageous to have an immutable storage of a digital record of medical events that are paired with the patient or recipient, the provider or healthcare worker, as well as the facility and location whereby the event took place. This immutable record could then be accessed by additional stakeholders in a secure manner such as using a biometric key or unique secure token. The token or key could be given to future medical providers, insurance or other administrative processes, or access by the patient or other stakeholder themselves for future reference upon authorization.

The medical, pharmaceutical, and drug manufacturing industries are one of the most regulated business segments. Misrepresentation fraud and errors can lead to injury and even unnecessary death. A system that has improved verification and does not rely upon "trust" of the human operator or human input generated data would be desirable. The insurance industries are also rocked with fraud bloated management and oversight costs in multiple entries related to claims billings services provided. A platform that requires only a matching biometrically and that can automate autonomously the entire payment and confirmation process by verifications of when where and what and by whom would again be of great value.

It would be advantageous to have an immutable storage system whereby a built in auditing engine could confirm the data records being created. The data records being immutable would be verified as to the accuracy and confirmation of hashes or other means of immutably recorded in the data as well as the data contained in the hashes being accurate. The data obtained could then be used for predictive analytics or as well for analytical processes to help improve medical treatments and patient experiences.

SUMMARY OF THE SYSTEM

In accordance with an exemplary embodiment, this system a computerized system for verifiably pairing a medical event. A medical object can be any one of or a combination of a medical device, medication, application of a medical device, administration of a medication, diagnosis, treatment, and procedure. A medical device can be a prosthetic, implant, medical tool, test kits, monitors, diagnostic devices (e.g., MRI, x-rays, etc.). A medical object can be robotic, automated, manual or a combination. This system pairs a medical object with a digital representation comprising is provided and adapted to include a kiosk having a computer system disposed at a use location and in communication with a persistent storage. The system can include a medical object with a unique identifier; a set of non-transitory computer readable instructions included in the computer system adapted for: retrieving, from the persistent storage, a supplier record created by a supplier according to a first verification representing verification that a medical object and its accompanying specifications and requirements is paired with a first virtual representation stored on the persistent storage, associating regulatory information with the unique identifier wherein the regulatory information is associated with the use location and wherein the regulatory information is taken from the group consisting of location, date, time, event, task, individuals, approval, and any combination, creating a medical object record having the unique identifier and according to the supplier record and the regulatory information, and, storing the medical article record in the persistent storage.

The medical object can include articles taken from the group consisting of a raw material, chemical, compound, medical device, medication, and medical container. The use location can be taken from the group consisting of laboratory, testing facility, medical facility, healthcare provider facility, manufacturing facility, distribution facility, pharmacy, sales location, and any combination thereof. The medical object can include a shipping information received by the kiosk from a shipper computer system and the shipping information can include a second verification representing that the medical article received at the use location is the same medical object send by the supplier and received at the use location. The verification can be a visual inspection by an individual and recorded in the system to provide verification and authentication information between the physical article and the digital representation. The medical object record can include a material information representing the material used to make the medical article and a third verification representing that the medical event includes the material represented by the material information. The regulatory information can include biometric information of an individual inspecting the medical article during a regulatory approval process. This regulatory information can include verification that the manufacturing, storage, distribution, individual (and licenses), dispensing (dosage, frequency, patient, and the like) and any combination thereof. The notation of the regulatory information is an industry standard compliance representing that the medication or medical device was made, distributed, used or otherwise within regulatory standards and requirements.

The non-transitory computer readable instructions can be adapted to retrieve the medical event record, receive a recipient information, receive a distributor information, associate the virtual representation with a transaction according to the recipient information and the distributor information, create a transaction record according to the transaction, medical object records and transaction verification information. The transaction verification information can be taken from the group consisting of a visual information, biometric information of the recipient, biometric information of the distributor, recipient identification, verification of the distributor, verification of the medical article and any combination. The medical object can be associated with verification information that can include capturing an image taken of the medical article at a transaction location, transaction date, transaction time, transaction event, recipient, distributor, or any combination thereof. The transaction location can include a location marker associated with the location; and the kiosk is uniquely paired with the transaction location using the location marker. The supplier record can be created according to a physical verification of a first tag affixed to the medical article. The supplier record can be created according to a physical verification of a first tag affixed to a container adapted to receive physical articles associated with the medical object. The set of computer readable instructions can be adapted to creating a recipient record representing the recipient of the medical article and storing the recipient record on the persistence storage.

The system can be adapted to provide for a computerized system for pairing a medical object with a digital representation comprising: a computer system disposed at a use location and in communications with a persistent storage; a sensor in communications with the computer system; a set of non-transitory computer readable instructions included in the computer system adapted for: creating a medical object record using the sensor representing the medical article that is paired with a virtual representation wherein the virtual representation is included in the medical object record, creating a regulatory record using the sensor having significance information taken from the group consisting of date, time, event, individual, and any combination, associating the regulatory record with the virtual representation, and storing the medical article record and the associated regulatory record on the persistence storage.

The regulatory record can represent the regulation requirements for a medical device, treatment, or medication. For example, certain medications can only be distributed at certain intervals. The system can determine if a patient has received a medication outside these regulatory requirements. The regulatory record can include information from the regulatory agency, healthcare facility or other source. The regulatory requirements can include restriction of use of the medical object based upon the patient, test subject, test criteria, drug interactions, or other criteria associated with the medical object and its use.

The medical article record, and the associated regulatory record can be configured to be retrieved from the persistent storage from a third-party computer system providing for verification that the medical article is authentic according to the medical article record and the associated regulatory record. The computer system can be a kiosk or can be contained in a kiosk.

The system can include a computerized system for verifiably pairing a medical article with a digital representation comprising: a computer system disposed at a use location and in communication with a persistent storage; a sensor assembly in communications with the computer system; a medical article associated with a unique identifier; a set of non-transitory computer readable instructions included in the computer system adapted for: creating a medical article record using the sensor assembly representing the medical record that is paired with a virtual representation, associating a regulatory record with the virtual representation storing the medical article record and the associated regulatory record on the persistence storage, creating a transaction record representing a transfer of the medical article from a first entity to a second entity wherein the transaction record includes a transaction verification, transmitting a payment request according to the transaction verification to a second entity account representing payment for the medical article from the second entity to the first entity, and, storing the medical article record and the associated regulatory record on the persistence storage. The regulatory record can include information taken from the group consisting of date, time, event, individual, testing, compliance, and any combination. The identifier can be taken from the group consisting of a serial number, bar code, QR code, RFID, beacons, lot, tag, image, microdot, material information, container information, and any combination thereof.

The non-transitory computer readable instruction can be adapted for creating a transaction record representing a physical verification of a transfer of the medical article from a manufacturer to a second entity. The non-transitory computer readable instruction can be adapted for transmitting a payment request according to the transaction record to a second entity account representing payment for the medical article from the second entity to the manufacturer.

This system can also capture, pair, and store medical treatments as well as medical devices and medications. In the case of the medical treatment, the system can capture the medical treatment process in digital form which can then become the article that is being verified and stored. The system can include in the records associated with the medical object including medica device, medication or medical treatment, information that is captured from third party device such as blood pressure, weight, heart rate and other medical devices, including those designed to communication through IoT and any combination.

This system can include hardware that can be adapted for autonomously (e.g., IoT) collect such things as patient vitals which would eliminate human error or misrepresentation.

BRIEF DESCRIPTION OF THE DRAWINGS

FIGS. 1A-1F shows various side views of aspects of the system.

FIG. 6 shows various types of biometric data that may be gathered.

FIG. 7 shows the types of events that may be triggered.

FIGS. 8-11 shows a flowchart illustrating aspects of the system.

FIGS. 14-22 show flowcharts illustrating steps of the system.

DETAILED DESCRIPTION

Figure 1D:
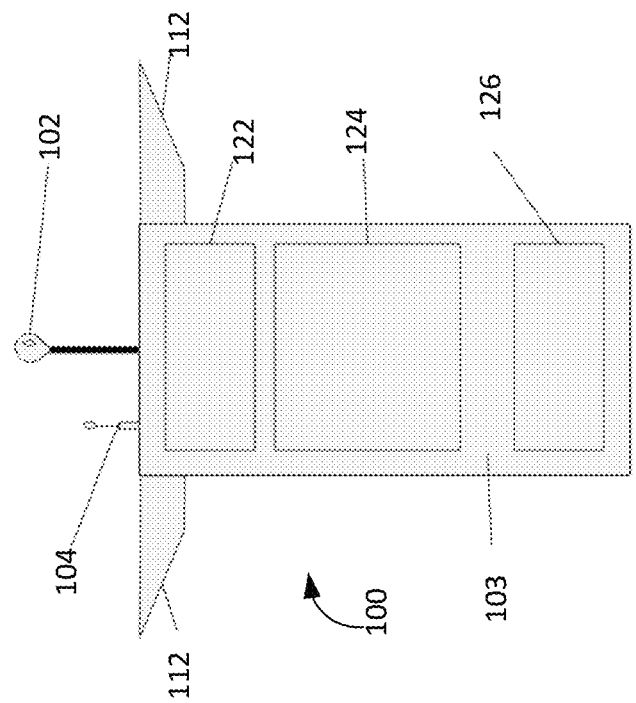

The present system provides for real time verified pairing of medica object that can include physical article or task such as medical research, medical treatments, a medical device, testing, clinical trials, and a medication with a virtual (e.g., digital) representation. The server or kiosk can include a set of server computer readable instructions configured to receive information about an article or task that can include the ability to capture information such as research, description of the article, task or process, manufacturer, characteristics of the article or task, process, procedures, materials, and the like, an event associated with the article or task, its significance, the individuals associated with the article or task such as researchers, shippers, manufacturers, distributors, medical service suppliers, dispensaries, medical facilities, date and time, location, individuals that can verify or certify the generation of the digital representation and the meta data associated with the article of task.

For example, the system can capture an image of the object or task, its unique identifier and associate that information with a date, time, and location. Individual can be captured that can include images, video, date, time, and location information of the individuals. An inspector can visually inspect the article or observe the task and verify that the article or task and individual were at the location at the same time to increase confidence in the authenticity of the article or task. The system can retrieve scheduling and occupancy information and verify that the individuals involved were at the same location at the stated date and time. Images of the article or task can be compared with environmental information (e.g., weather) information at the location, date, and time so that the background of an image showing the environmental conditions can be compared with third party weather information. If the image of the article shows a cloudy date and the third-party weather information shows a cloudy day, the confidence of the virtual representations of the article increases. Biometric data can be capture from the individual as well as attendance information from access control system to verify that the individual was at the use location at the date and time the virtual representation is retrieved, created, and stored.

The information captured can be stored in a record that include fields associated with the above as well as individuals involved, observers, materials used, equipment used, processes used, location, date, time, results, warrant information, class, type, lot, batch, or other identification of the article or task, one or more sources, cost, care instructions, material specifications, shipping information, storage information, and other information. The article record may be created or updated as actual articles arrive to a location and have serial numbers, bar codes, QR codes, RFID values, beacons, lots, sizes, or other components or material identification added or associated with the article record. A task record can be created or updated to include tasks associated with article such as research, reactions, processes, procedures, manufacturing, packaging, shipping, storage, testing, trials, and any combination.

Referring to FIGS. 1A-1D illustrate one embodiment of a system 100 that can be a kiosk of other housing that can be uniquely associated with a use location. The computer system that is included in the housing can also be removably connected to the housing and can be a portable computer device. If the computer device having the controller is a portable computer device, the portable computer device can be physically attached to a use location, virtually associated with a use location, or can be identified as being at a use location (e.g., using global positioning coordinates) when data is captured with the compute device so that the date, time, data, and location are associated at the time of data capture.

The housing can also be affixed to the use location. The system can be implemented as a kiosk that can be mobile and include a housing having a controller. The housing 103 may be located at a use location and include a controller in communications with a computer readable medium. The housing can be physically associated with the use location, virtually associated with the use location or both. A location marker can be affixed to the use location such as in a concrete slab, placard, label or otherwise affixed at the use location. The housing can be removeable attached to the use location so that it is stationary during a first task process but can be moved to a second task or process at a different physical location once the first task or process is completed. For example, the housing can be positioned at a research lab for collection of data and then at a testing facility subsequently.

For a location marker, a transmitter such as a RFID can be associated with the use location by embedding it is a permanent fixture such as a concrete slab, foundation, structure, and the like. The system can read the information from the location marker and associate its actual location with the use location. The location marker can include an alpha, numeric or graphical information such as a number, letters, barcodes, QR code, physical or geographic coordinates (e.g., GPS coordinates), passive transmitter, active transmitter, and the like. Each system can have a unique identifier and each use location can have a unique identifier.

FIG. 1A shows a first side of the system 100. The system 100 can include a camera 102 for obtaining images of articles, individuals, or other items at, entering, or leaving the use location as well as images of individuals along a perimeter. The camera 102 may capture biometric images upon which biometric recognition may be performed. Multiple cameras may be placed on or around the housing. The cameras may have biometric recognition and motion detection capabilities. System 100 may include an addition to the camera 102 or instead of the camera 102, biometric-based identification devices that may be used to confirm the identity of individuals entering, leaving or on the perimeter of the use location. The system 100 may include an antenna 104 for communicating with a network including a wireless network, Wi-Fi network, Bluetooth, quantum networks, cellular network (e.g., 4G or 5G network) and any combination. The system 100 may include a housing 103 made of suitable weather resistant material, appropriately sealed to protect the internal hardware. The system 100 may include a display 106A, such as a touchscreen display, upon which information may be displayed and entered. The display 106A may include an integrated camera that may be used to capture images and that may be used in performing facial recognition of individuals and other material. The display may also include or be operatively associate with one or more integrated speakers for providing audio output, a microphone for receiving audio information to facilitate two-way communications to a remote location. The system 100 may include a scanner 110A for scanning items, such as deliveries, as will be explained in more detail below. The scanner 110a may be, for example, a QR scanner, an Optical Character Recognition (OCR) or a bar code scanner 110A in some instances. The side of the system 100 shown in FIG. 1A can be used for deliveries and dispensaries. A delivery person may scan delivered materials, equipment, medical device and components, medicines, or other items via the scanner 110A and may interface with the system using the touch screen display 106A. An individual may scan or take images of items related to an inspection such as inspection documents via the scanner 110A or camera and may interface with the system using the touch screen display 106A. In some embodiments, there may be fewer sides in which to interact with the system for all authorized personnel. In some embodiments, the controller or kiosk can be wall mounted. An overhang 112 may be provided to assist in decreasing glare and protecting some of the items on the housing from the weather. The above components can be included in a sensor assembly in communications with the controller.

FIG. 1B depicts a side of the system 100. This side can include a touch screen display 106B as well as a scanner 110B. Display 106B may include or be operatively associated with an integrated camera for capturing images, speakers for providing audio output and a microphone to facilitate two-way communications with a remote location. Still further, this side of the system 100 may include data ports 1088.

Figure 1C:
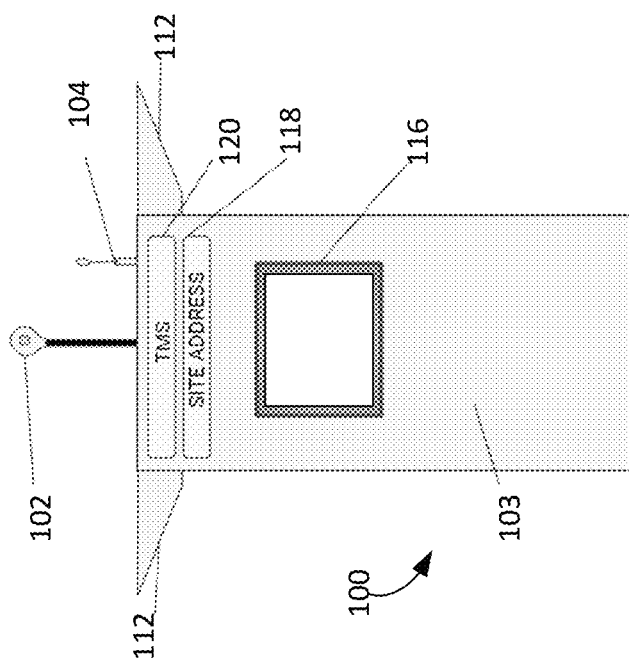

FIG. 1C shows a third side of the system 100. This side has a location 116 in which information such as notes, reports, results, status of task (e.g., tests, manufacturing, bill of sale, receipts, tax information, device application, and the like may be displayed. In some embodiments, the information displayed may assume electronic form so that a video display is provided in the area 116 of the housing 103.

In one embodiment, the unique identifier can be a number 120 for the use location may be displayed on the housing 103. Other location identifying information can be displayed such as location number, store number, assembly number, trade show number, certification number, use location and the like. In addition, the site address 118 may be displayed on the system 100. The site address may refer to both the mailing address for the use location and other physically identifying information associated with the location.

FIG. 1D shows a side of the system 100. An access panel 122 may be provided to access a breaker box for the system 100. An additional access panel 124 may also be provided to access internal components of the system 100.

Figure 1F:
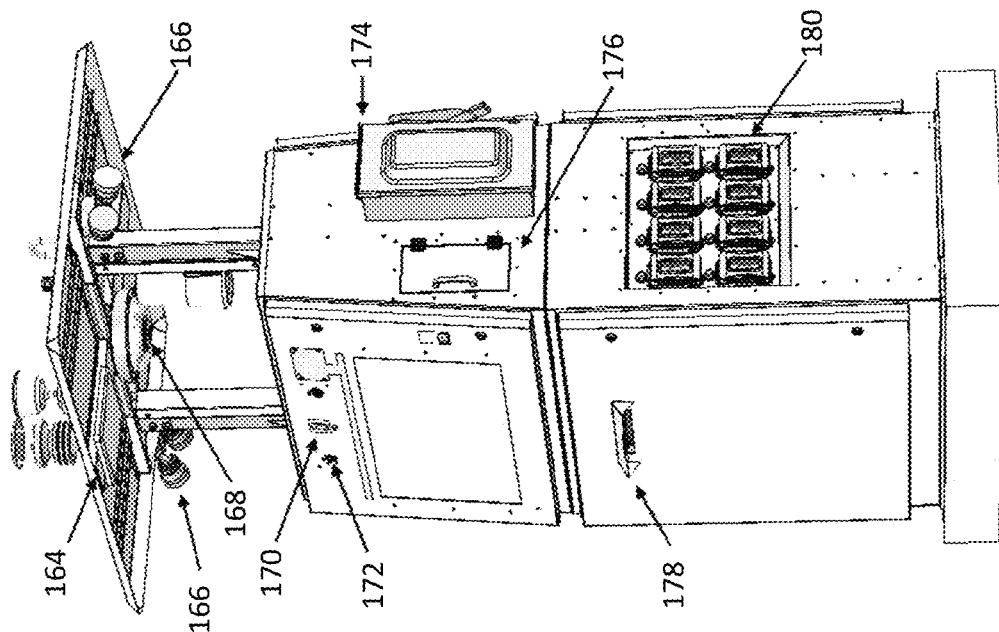
Figure 1E:
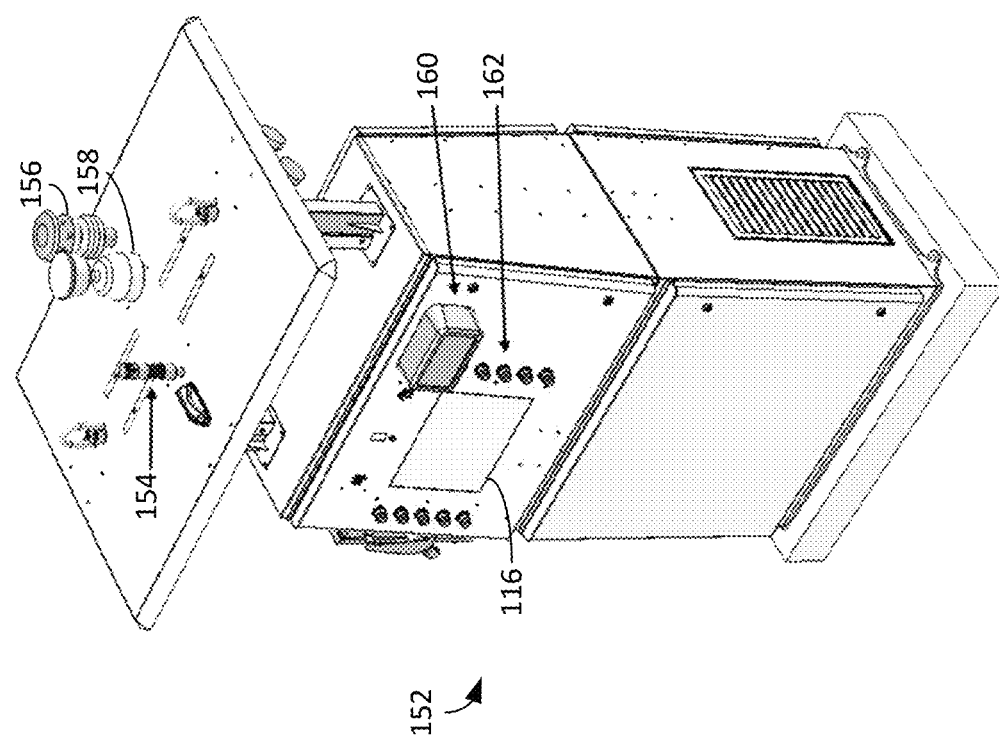

Referring to FIGS. 1E and 1F, the housing 152 can include a side that is configured to be used by an individual at the use location. The housing can include an alarm indicator 154 that can be actuated as described herein. The housing can include environmental sensors for collecting information such as temperature, humidity, air quality, air pressure, and the like. The housing can include input for receiving information from third party sources such as testing equipment, manufacturing equipment, access control systems, accounting systems, workflow automation systems, quality control systems, peer review systems, air condition system, building control systems, scheduling systems, and the like. Biometric reader 160 can include an iris scanner, fingerprint scanner, palm print scanner, facial scanner, or some combination. Display 116 can be proximity to input assemblies such as physical or contactless buttons 162 of facial recognition or other sensor. The housing can include a field receiver 164, lights 166 and camera 168. One or more cameras can provide a 360° field of view and include a wireless connection for transmitting images to a remote computer device. The images can also be used for input to the system including input allowing the system to identify delivered tasks and materials. The system can include one or more second cameras 170 such as webcams disposed at various locations around the system for capturing images. The lights can include motion activation and photoelectric activation. Speakers 172 can be included to provide audio information to a user, inspector, or other party using or near the system. The audio information can include instructions, alarms, and the like. Power junction 174 can include a shut off switch that can be used in emergency and non-emergency situations. The power junction 180 can be used for providing power to system including testing equipment, access control, medical equipment, diagnosis equipment, and the like. The system can include a secondary power source, such as a battery, so that when the main power is shut off, an alarm can sound, notification send to a remote computer device of other indication that the system or power source has been powered down. The system can include a hand scanner (not shown) that can be protected by a hand scanner access door 176. A document scanner 178 can be included in the system for receiving physical documents, converting the physical document into a digital representation, and storing the digital representation on the computer readable medium or the persistent storage. The system can include a wired connection to remote computer devices of a transceiver to provide a wireless connection to remote computer devices.

Figure 1G:
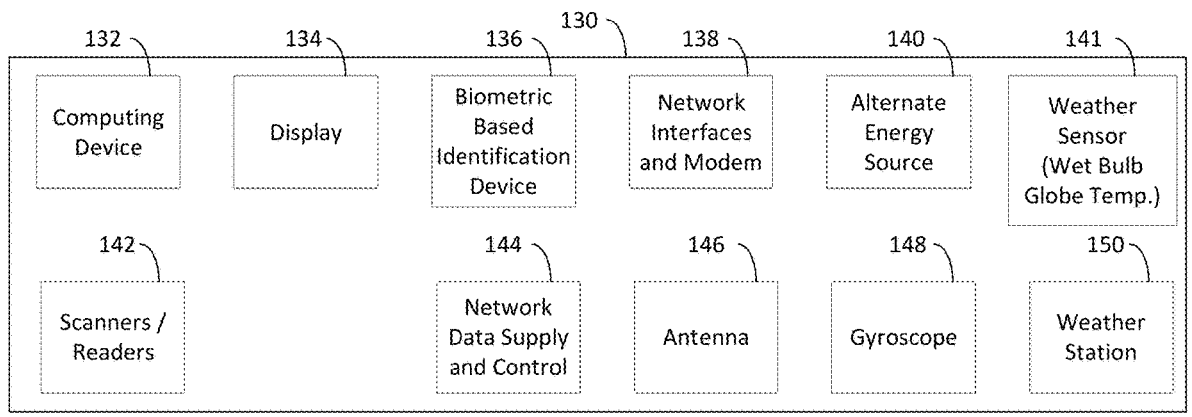
FIG. 1G is a block diagram of components of aspects of the system.

FIG. 1G depicts components that may be included in the system of exemplary embodiments even when not included in a housing. The system may include a computing device 132. The computing device 132 may take many different forms indicating a desktop computing device, a laptop computing device, a mobile computing device, an embedded system, a smartphone, special computer device, custom computer device, or the like. A display 134 may be integrated with the computing device 132 or as a separate device, such as a liquid crystal display (LCD) device, a light emitting diode (LED) display device or other types of display devices on which computer information may be displayed. One or more biometric-based identification devices 136 may be provided. As will be explained in more detail below, multiple biometric-based identification devices may be used. Network interfaces and a modem 138 may be provided. The network interfaces may interface the computing device 132 with a local area network or a wide area network wherein the networks may be wired or wireless. A modem may be provided to communicate telephonically or over cable lines with remote computing devices.

The system 130 may be implemented in a distributed fashion and may include an alternative energy source 140. For example, solar panels, wind turbine(s), a battery or the like may be used. In one embodiment, the alternative energy source may be physically affixed to the housing or in communications with the system or controller. For example, solar panels or a cable to a wind power source could be configured to provide power to the system and can be affixed to the system or housing. Alternatively, a power line leading to the alternative energy source may be connected to the housing and system to provide power to the system, housing, and associated components such as external power supplies.

The system 130 may include various scanners and readers 142, such as those described above relative to housing. The system 130 may include an internet data supply control 144 and a mechanism for turning the access to this service on and off under a programmatic control. Programmatic control may be provided to grant or deny access to such resources including medical equipment, storage areas, and diagnostic equipment. The system 130 may include an antenna 146 for wireless communications signals to receive and transmit. The system 130 may include a gyroscope 148 to monitor any moving of the system. The gyroscope 148 may indicate motion indicative of whether someone is trying to move or tilt the housing or other component of the system. Logic may be provided to send a notification in such an event where the gyroscope indicates substantial enough movement. The system 130 may include a weather or environmental station 150 to measure current environmental conditions, such as temperature, air movement, humidity, precipitation, barometric pressure, direct sunlight, and the like. Input from the station 150 may be used to inform decision making by the system in some instances. Alternatively, the environmental conditions may be collected via software, such as from a weather service, building system, air conditioner, or other sources. Similarly, the system 130 may include a fluid sensor 141.

Figure 2A:
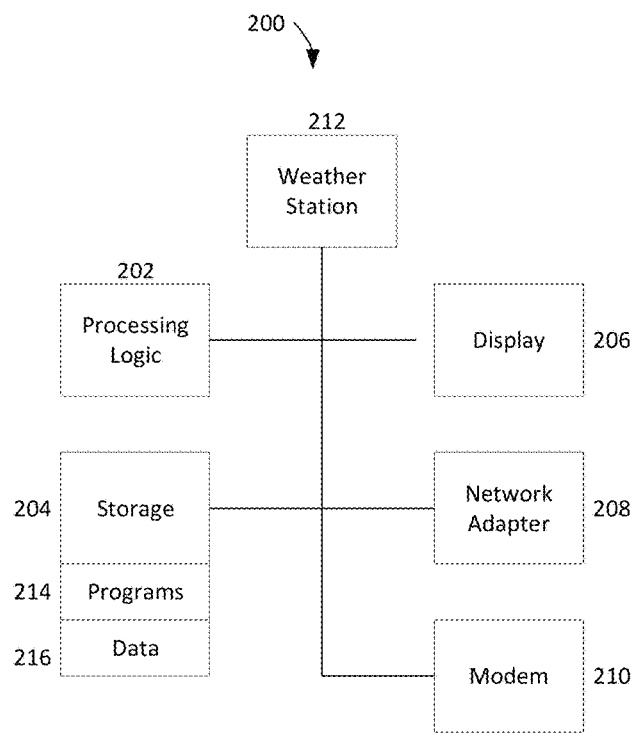
FIG. 2A is a block diagram of aspects of the system.

FIG. 2A shows an example of a computing device 200 for the system. The computing system may include processing logic 202, such as microprocessors, controllers, field programmable gate arrays (FPGA), application specific integrated circuits (ASICs) electronic circuitry, and other types of logic. The processing logic 202 performs the operations of the computing device 132. A storage device 204 may also be provided. The computer readable medium and data storage device 204 may take various forms, including magnetic storage, optical storage, etc. Storage capability 204 may include computer-readable media, including removable computer readable media, such as disks, thumb drives and the like, or disk drives, solid state memory, random access memory (RAM), read only memory (ROM) and other types of storage. The computing device may include a display 206, such as an LCD display, an LED display, or other types of display devices on which video information may be displayed. The computing device 200 may include a network adapter 208 for interfacing with networks and a modem 210 for communicating wirelessly, over telephone lines or cable lines with remote devices. The processing logic 202 may use information stored in the storage device 204. In particular, the processing logic 202 may execute programs 214 stored in the storage and may access and store data 216 relative to the storage device 204. The computational functionality of the system described herein may be realized by the processing logic 202 executing the programs 214.

Figure 2B:
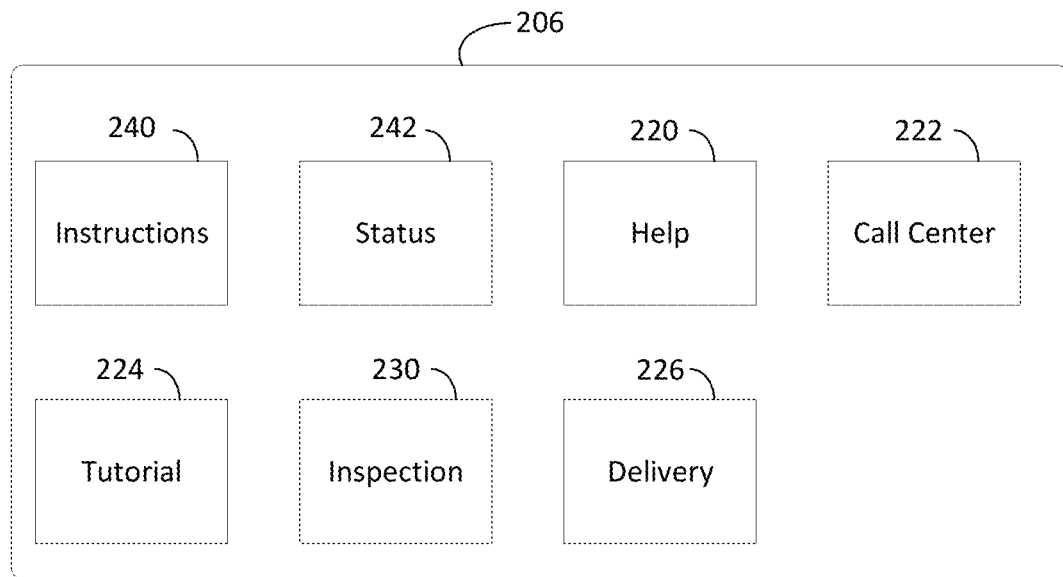
FIG. 2B shows aspects of a user interface.

FIG. 2B shows an example of a user interface on display 206, such as found in the housing 100. The user interface may include activatable elements. A user may depress these activatable elements or select these activatable elements using an input device, such as a probe, sensor, mouse, keyboard, touchscreen, or the like, to activate the components. The display 206 may include a help element 220 that may be activated to obtain help information regarding use of the housing. It may also contain real time project or process plans. It may also include "how to" assistance including videos related to the various projects, stages, processes, and tasks performed at the use location. The user interface on the display 206 may also include a call center activatable element 222. Selection of the call center activatable element 222 may cause a call to be initiated with a call center so that the individual using the system 100 may have a telephone and or video conference with personnel at the call center such as used with telemedicine. The call center can be connected to several third parties including a prior authentication individual or entity if communications is needed. For example, a call can be made at a lab or manufacturing facility to verify or assist in the verification of a medical device or medication and if that article originated at the lag, manufacturing facility or otherwise. The user interface on display 206 may also include a tutorial activatable element 224. Selection of the tutorial activatable element 224 causes a tutorial to be displayed to teach the individual about operation of the housing.

Figure 2C:
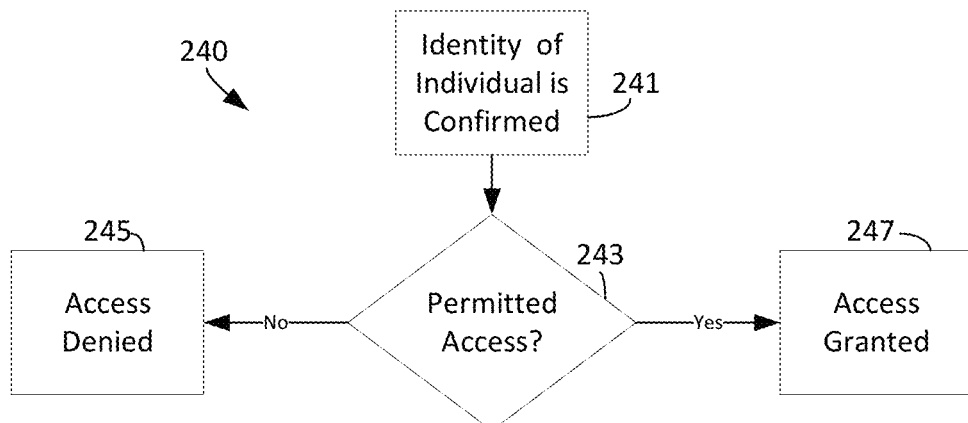
FIGS. 2C-2D show flowcharts of aspects of the system.

Referring to FIG. 2C, the display may show instructions 240 for completing certain tasks or other information. A status of tasks, material and articles can be displayed. For example, an individual can view the display and receive status information about a medical device or medication such as anticipated completion, testing, delivery, route information, current location, or tasks as well as the status of tasks including performance steps, start times, status, progress, results, competition times and the like. The identity of an individual can be confirmed at 241, such as described above using biometric identity verification. The individual's information is accessed to determine if the individual is to be granted access to the article at 243. If the permissions indicate that access is to be granted, access is granted 247. In contrast if the permissions indicate that access is not to be granted, then access is denied 245. Permission information can be included in the individual information record. Permission information can be retrieved from the persistent storage or the system.

Figure 2D:
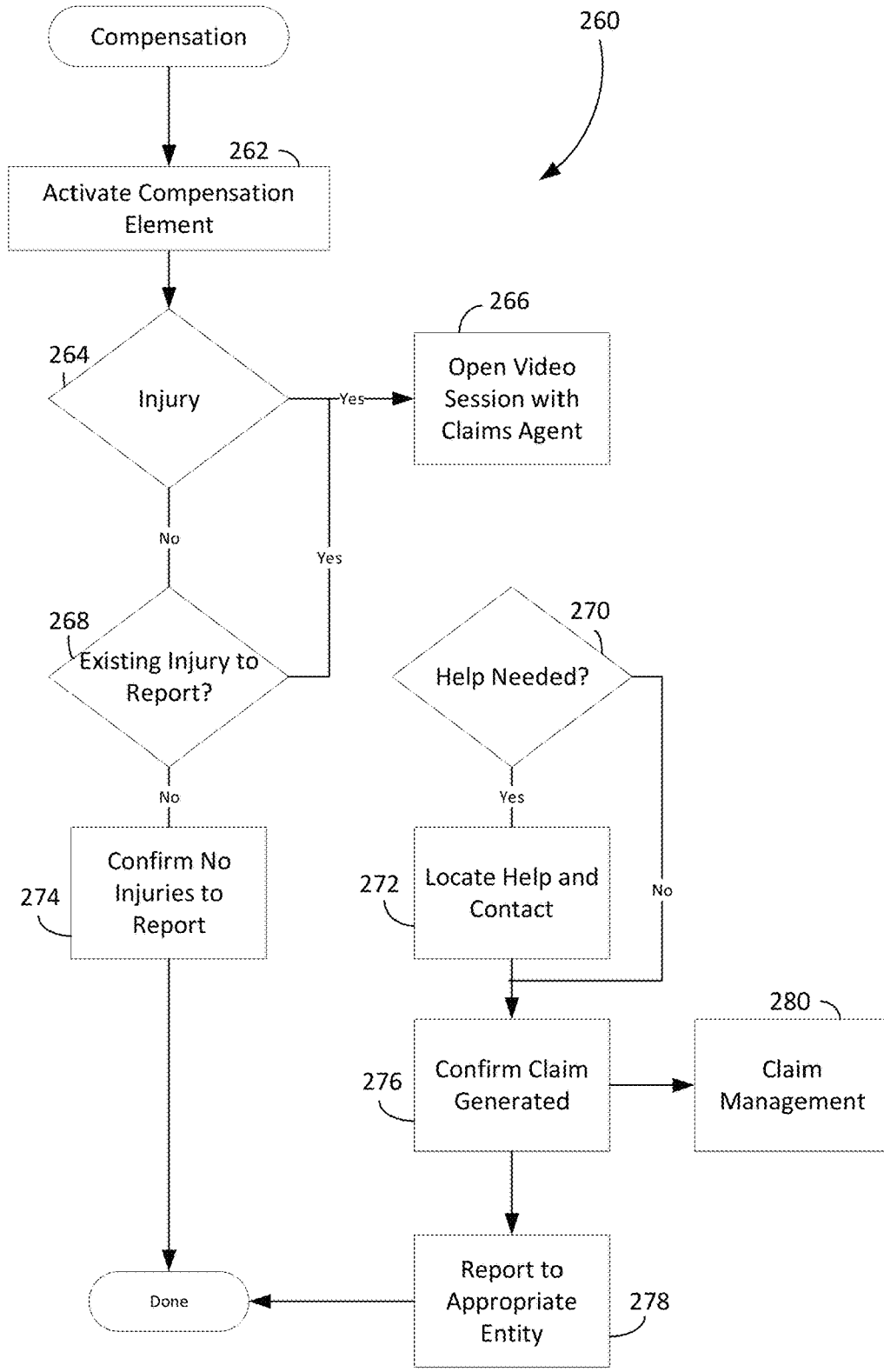

The system 130 can also allow or prevent access to the use location. When an individual arrives at the use locations, the selection of the individual compensation activation element 238 may be required at the beginning and end of each workday to track the individual. FIG. 2D provides a flowchart 260 of steps taken when the element is activated at 262. All individuals may be required to enter this information each day. If an individual indicates some type of injury, loss or claim at 264, a video session with a claim agent can be initiated at 266. For example, during a drug trial, the subject can report an illness, reaction, or other effect as well as being in good health, having no reaction or other effect of lack thereof to the trial administration. The claim agent may gather information to initiate any claim processing. The claim agent may determine if assistance is warranted 270. If medical help is warranted, the location of appropriate medical help can be identified based on a location of the use location (e.g., based on proximity and type of injury) and contact is made with the assistance 272. A confirmation of the claim can be generated 276 and sent to claims management 280. In addition, a report may be sent to the appropriate entity or authority at 278. The steps 266, 270 and 272 may also be performed in the instance in which the individual has an older injury to report 268. Where there is no injury to the individual, the lack of injury is reported 274. The process herein can be applied to injury to individuals, material, and equipment.

Shipping or delivery company personnel may activate the delivery activatable element 226 (FIG. 2B). This causes a delivery functionality to be displayed where delivery notes may be added and where information may be gathered from the delivery person regarding a particular delivery.

An individual activatable element may be selected by individuals. Selection of this activatable element causes the activation of the individual functionality whereby the individual may sign in, request materials, tools, equipment, power or materials and leave notes, record data and the like.

An inspector activatable element 230, may be activated to cause the inspector functionality to be activated. The inspector functionality may enable an inspector to add inspection notes, provide electronic inspection certificates, review results, review status of material, processes, tasks, equipment, and the like. The system can provide reports that can be automatically generated from the existing data described herein as well as notes manually added during the manufacturing and tracking process. The reports can be generated at predetermined times such as daily or upon completion of specific tasks.

Figure 3A:
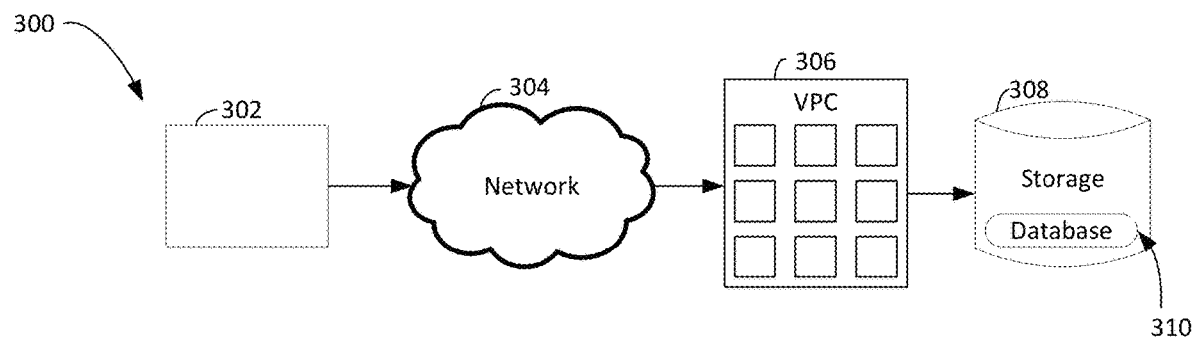
FIG. 3A shows an example of a communications environment.

As shown in FIG. 3A, the exemplary embodiments may be implemented in a decentralized computing environment 300, that may include distributed systems and cloud computing. FIG. 3A shows one or more systems 302 that may be in communication with a remote cluster 306 via a network 304. The cluster 306 may store information received from the system 302 and provide added computational functionality. The network may be a wired network or a wireless network or a combination thereof. The network 304 may be a secure internet connection extending between the system 302 and the cluster 306, such as a virtual private cloud (VPC). The cluster 306 may include access to storage 308. The storage 308 may include a database 310 in which information regarding a use location is stored in a consistent manner.

Figure 3B:
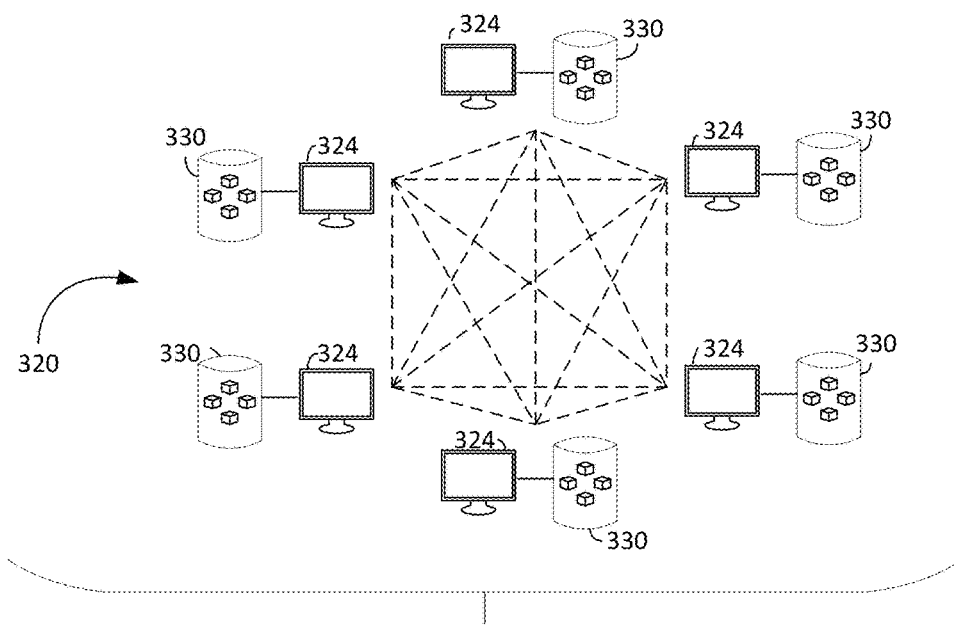
FIG. 3B shows an example of a persistent storage.
Figure 3C:
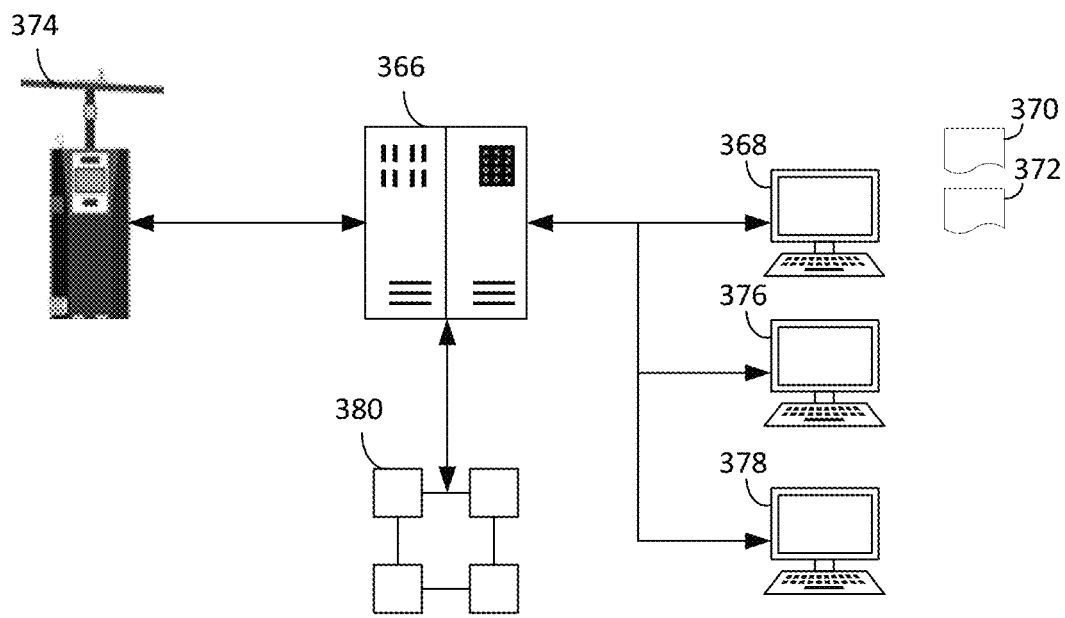
FIGS. 3C-3D show schematics of the aspects of the system.
Figure 3D:
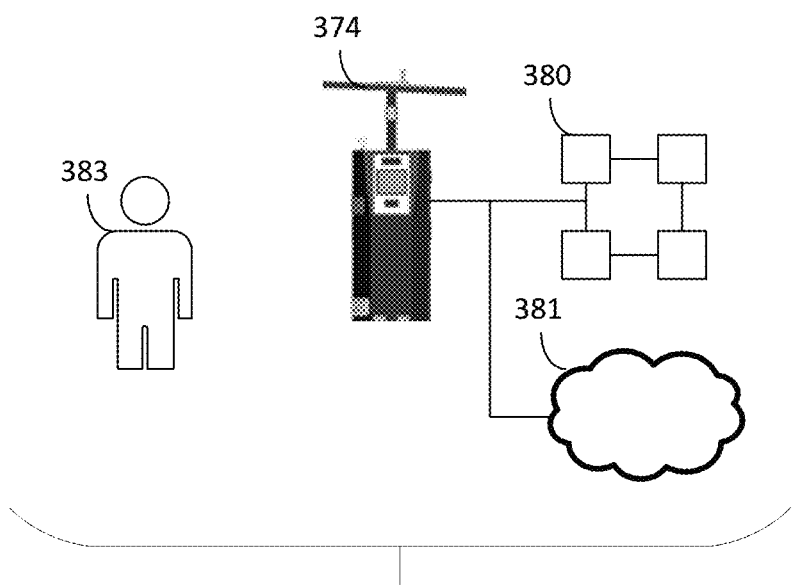

FIG. 3B shows diagram 320 of an example of a peer-based network where a persistent storage 330 is broadcast and shared among the nodes 324. This network may be resident in the VPC cluster 306 (FIG. 3A) or in the network 304 for example. The nodes 324 may represent computing resources, such as server computer systems or other computing systems with storage devices 330. FIG. 3C shows a kiosk 374 in communications with a server 366 that can be in communications with a distributed network 380 or computer, storage devices of any combination. Third party computer system 368, 376 and 378 can be in communications with the server 366 and kiosk 374 so that information 370 and 372 can be shared with these systems. FIG. 3D shows a user 383 using kiosk 374 to access information from distributed storage 380 as well as transmit and receive data from a global communication network 381.

The information from a research, lab, manufacturer, supply company or other third party can also be stored on the persistent storage and retrieved by the system. The housing can be configured for receiving a medical device record or a medicine record from the designer representing the medica device or medicine, creating an actual medical device or medicine requirement record representing the actual article delivered to the use location, creating a final medical device or medicine record (e.g., medical object record) according to a difference between the article requirement record and the article material record, receiving receipt verification information representing the actual article was received by an authorized individual 383 (FIG. 3D) and under a set of compliant environmental conditions, including weather conditions, receiving warranty criteria from the supply company representing the warranty requirements associated with the medical device or medication and their use, storage and the like and determining if the warrant criteria are met, creating a certificate of warranty according to the final material requirement record and installation verification information, and storing the certificate of warranty on the persistent storage.

Conditions associated with an article, task, use location, location marker, delivery, pick-up, individual, process, or task can include physical location (e.g., GPS coordinates), environmental conditions, impacted individuals, impacted materials, impacted equipment, date and time, duration, pre- and post-events (e.g., chronologically relevant action(s)), managers and supervisors on site and responsible.

Processes, projects, and task specifications, which may be needed for compliance with warranty, insurance, design, specifications, inspection, and other requirements, can be received at 376 and requirements can be received from a requirements computer device 378 either directly or from the persistent storage. The requirements can include approved materials that are approved by regulatory entities, such as governments, researchers, manufacturers, technicians, health care workers, distributors, designers, and the like. Requirements can include specifications, materials, safety codes, and individual licenses, and the like. The requirements can include processes and procedures for handling, use, installation, and assembly of the medical device or medicine.

The various computer devices, including the server and remote computer device (e.g., system, controller, and any combination), can be in communications with persistent storage 380. The persistent storage can include a distributed ledger, immutable database, block-chain structure, and the like. The communications between the various computer device, including the server and the remote computer device and persistent storage can be a global communications network, wide area network, or local area network, delivered to a computer readable medium from one device to another (e.g., USB drive, CD, DVD) and can be wired or wireless.

Figure 4:
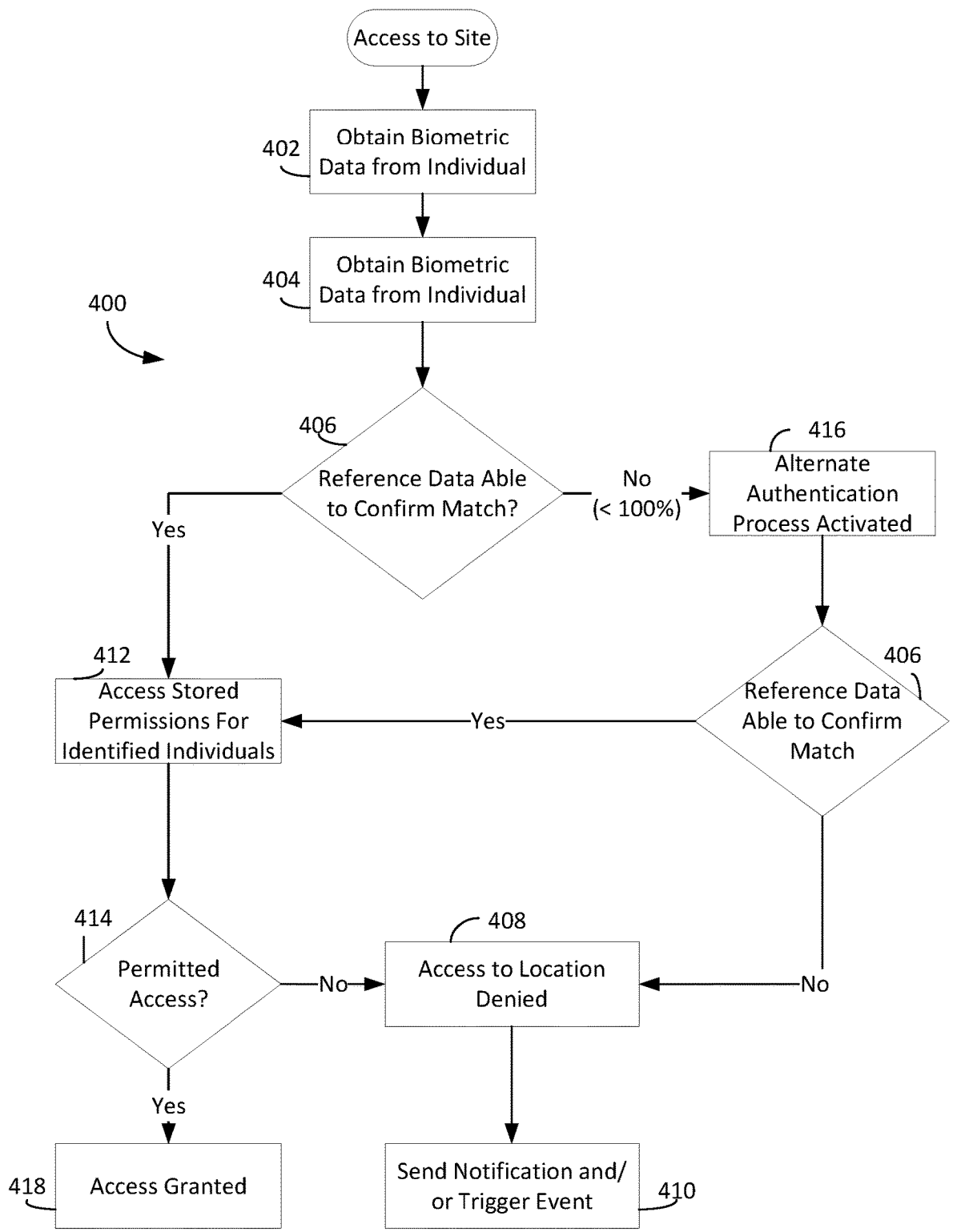
FIGS. 4-5 shows a flowchart illustrating aspects of the system.

FIG. 4 shows a flowchart 400 identifying steps that may be performed in exemplary embodiments regarding this functionality of the system. Initially, biometric data is obtained from an individual or other individual that is seeking access to the use location 402. In some exemplary embodiments, a camera 102 may capture an image of an individual and facial recognition may be performed. The biometric data in one case is the facial image of the individual. In other exemplary embodiments, the biometric data may be, for example, fingerprint data, hand scan data, voice print data, retinal scan data or the like, gathered by appropriate biometric-based identification devices. The obtained biometric data is stored, and then previously stored data is accessed from storage to compare biometric data for known individuals and to attempt to identify the individual 404. A comparison may be made between the gathered biometric data and the known biometric data to determine if there is sufficient closeness for there to be a match. Information regarding the identity of the individuals for which the biometric data is stored is also stored in the storage device. A determination is then made whether there is a match or not 406. An individual data can include the credentials of the individual and used to compare the access attempt with the record associated with the individual.

If there is not a match 406, a manual process may be executed, or an alternative authentication process may be deployed 416. If this alternative authentication fails to produce a match 406, access to the use location may be denied 408. In addition, a notification may be sent to a responsible party and an event may be triggered, such as contacting security or law enforcement officials 410 such as in the case of a attempted theft of medical devices or medications. If the alternative authentication process produces a match, the process proceeds to 412.

The system may store permissions for anyone allowed to access system and use location. These permissions may identify the dates and times where the individual is given access. In addition, the permissions may specify what materials, articles and tasks the individual can access or preform. These permissions may be accessed to determine the permissions for the identified individual 412. If the permissions indicate that access is permitted 414, the individual may be granted access to the use location and article at 418.

Figure 5:
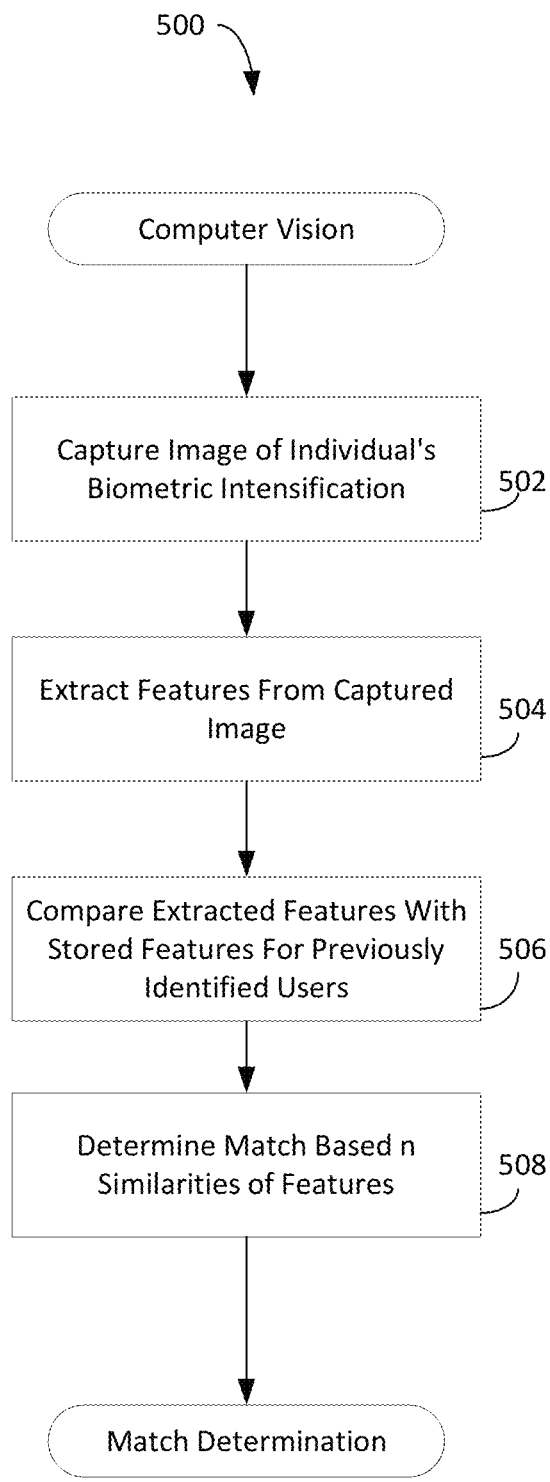

FIG. 5 shows steps that are performed in a case of computer vision for 402, 404 and 406 of FIG. 4. The flowchart 500 begins with 502 in which an image of an individual is captured for biometric recognition. This may be captured by a number of different types of image capture devices, including an intermittent video camera, still camera, iris scanner, facial scanner, fingerprint scanner, or other type of capture device. In the case where an image of the face of an individual is captured, identifying features may be extracted from the captured image 504. In other words, unique facial features that help to identify an individual are extracted from the image. The image may be filtered and normalized. The features are then compared with the stored features for identified individuals 506, determination is made whether there is enough similarity for there to be a match.

FIG. 6 shows a diagram 600 that illustrates various types of biometric data 602 that may be obtained by biometric-based identification devices at the use location to attempt to identify individuals. Biometric data may include facial recognition 603, an iris/retinal scan 604, a fingerprint scan 606, a hand scan 608, a voice print 610 or heart rate signature 614. It should be noted that other types 612 of biometric data may also be used in exemplary embodiments to help identify individuals uniquely. Also, an individual may be required to provide multiple types of biometric data in some instances.

When individuals attempt to access the use location and are not granted access, certain events may be triggered (see 410 in FIG. 4). FIG. 7 shows a diagram 700 that provides an example of different types of triggered events 702. One type of triggered event is an alarm 704. This alarm may include visual alerts, audio alerts and any combination thereof. The alarm may be a silent alarm to individuals. Another event that may be triggered is to send notifications to a supervisor for the use location 706. The supervisor may, for example, receive an email, a text, a phone call, or another notification that someone is trying to access the site that is not permitted. A triggered event 702 may also include the contacting of law enforcement or a member of a security service indicating that an unauthorized party has tried to access the use location. A triggered event 702 may include prompting the individual to produce proper identifying information to an official at the site or to a scanning device at the housing 100.

FIG. 8 shows a flowchart of the steps that may be performed to ensure that an individual gains access to the appropriate items once they have been granted access to the use location. As shown in the flowchart 800 of FIG. 8, initially the individual has their identity confirmed, as has been discussed above 802. The system may offer an alternative touchscreen option to place a call to the appropriate party should the software fail to verify and otherwise authorized the individual. The individual may be prompted to interact with the display, such as the touchscreen 106B (FIG. 1) to register and to indicate whether they seek certain items. For example, with the user interface of FIG. 2B, the individual may activate the individual activatable element 228. Access is then granted to wearables and tools and equipment 806.

FIG. 9 provides a flowchart 900 of the steps that may be performed relative to smart locks at the use location that can control access to areas, storage, devices, and the like. The individual has his/her identity determined and has access to the use location 902. The system may offer an alternative touchscreen option to place a call to the appropriate entity or location should the software fail to verify an otherwise authorized individual. The permissions stored for the individual are accessed 904. A determination is made whether the individual is granted access to a smart locked area 906. If the individual has permission to access the area 908, the smart locks may be de-activated to unlock the area, storage location or other place such as where articles including medical device, medication and materials are located. Before the individual can access the article, the individual may first be required to wear some of the wearables or have another identifier. If the individual lacks the proper permissions to access the article or location, then access can be denied 910, such as by keeping the smart locks locked.

Figures 10, 11:
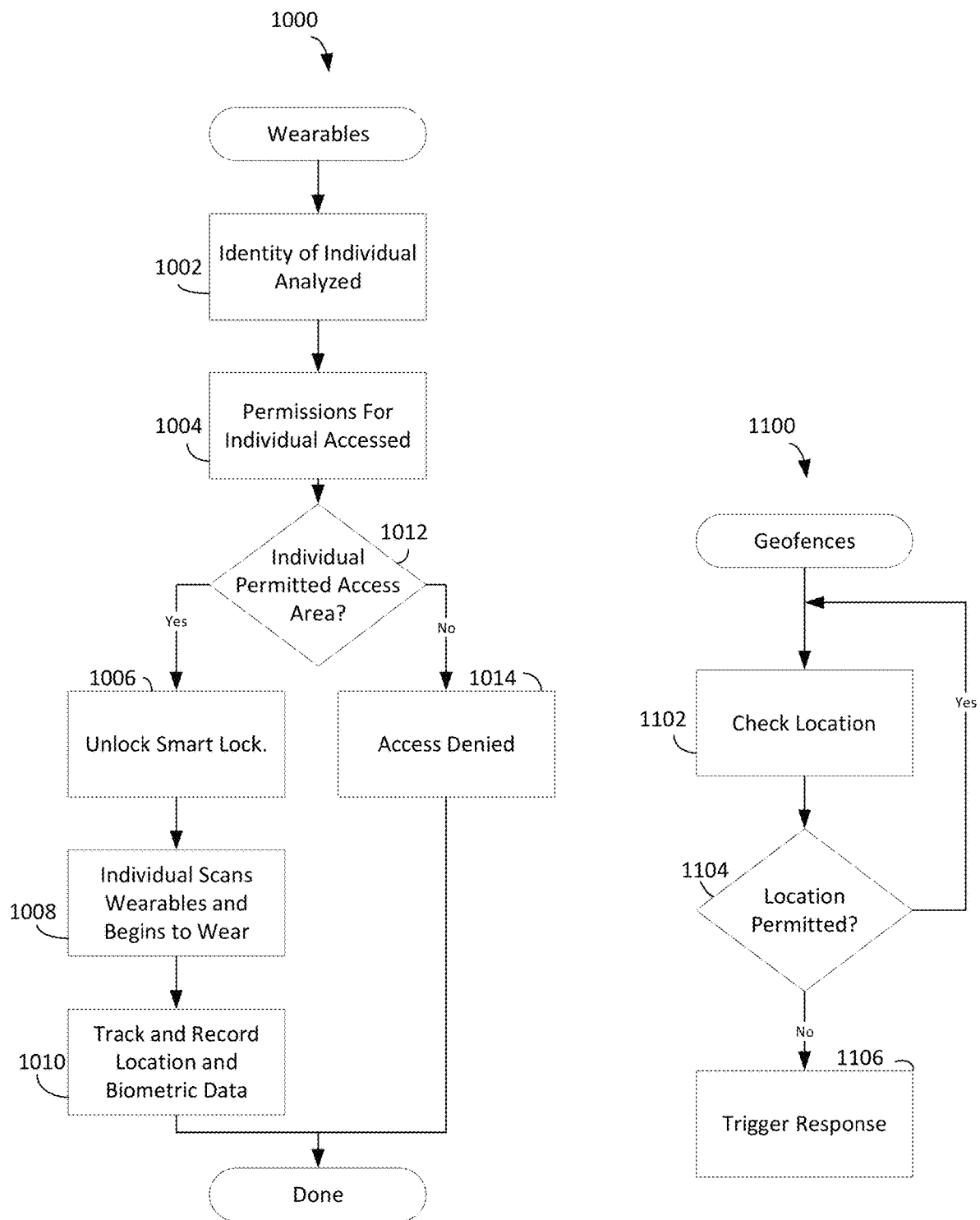

FIG. 10 contains a flowchart 1000 illustrating the steps that may be performed to obtain a wearable or other identification associated with an individual such as a manufacturer or health care provider. For some individuals, a wearable can be provided to the individual prior to interaction with the system and used to register with the system. This individual can receive the wearable and upon approaching a housing, be registered with the system when the individual reaches a certain proximity to the system.

The identity of the individual is confirmed 1002, and the permissions for the individual are accessed 1004 and a determination is made based on the permissions if the individual should be granted access to the wearables or other identification 1012. The system may offer an alternative touchscreen option to place a call to the appropriate party should the software fail to verify an otherwise authorized individual. If it is determined that the individual should be granted access, the smart lock for the storage location of the wearables, identification, or access article (e.g., badge or card) is unlocked 1006. The individual may then be prompted to scan information regarding the wearables or other item to register the item and associate the item with the individual 1008. In one embodiment, the system may use one or more images of an individual to determine if the individual has the necessary personal protection equipment.

The system tracks and records the location and biometric data gathered by the wearables 1010 or other identification item. The identification item may include smart vests, bracelets, badges, sensors, card, and the like. The identification item can include the ability to provide location information and biometric data, such as heart rate, body temperature, blood pressure, breathing rate, gyroscopic informatic and other information associated with a patient, participant, or healthcare provider. The identification item assists the system in tracking the location of individuals at the use location. The identification item also helps to track the biometric data of individuals. The biometric data may be helpful in identifying that an individual is experiencing an accident, a health event or is idle. The biometric data is stored so that a record of the biometric data can be kept. If in 1005, it is determined based on the permissions that the individual should not be granted access, then access to the identification item is denied 1014.

Figure 12A:
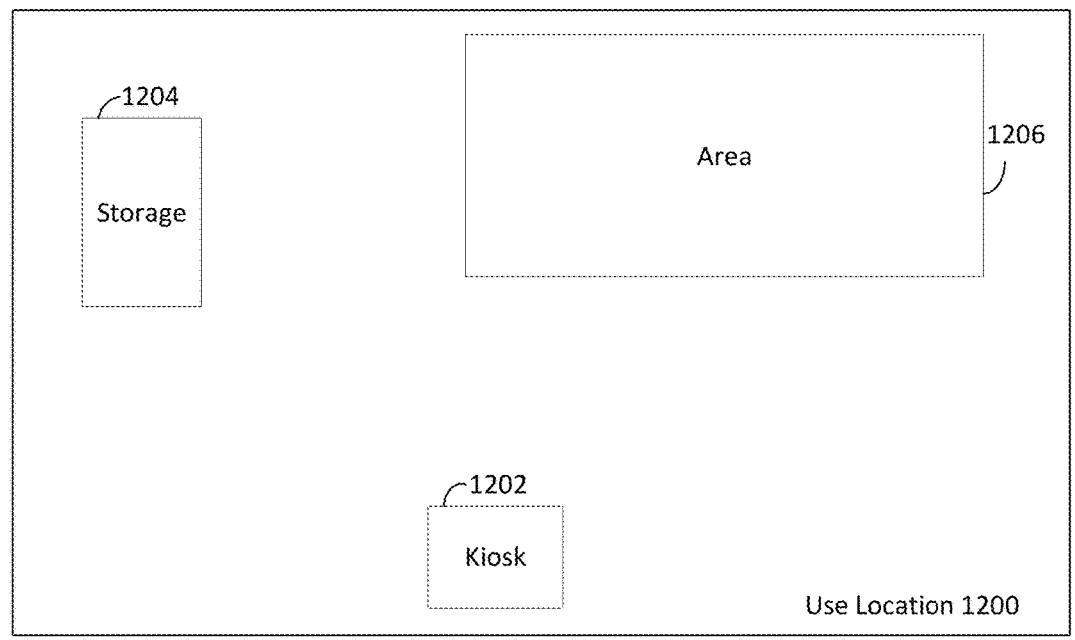
FIG. 12A shows a plan view of a use location.

The use of the identification item to track location helps to facilitate use and application of medical objects to determine warranty requirement compliance that may accompany a medical device. The identification item information can be combined with geofencing in an exemplary embodiment. The geofencing enables the system to track and limit access to locations of individuals at the use location and can designate storage area, testing area, treatment areas, including secure storage areas for medical devices, equipment, treatments, and medications. The use location may be partitioned into areas where different permission rights are given for the various areas. For example, a pharmacist can be given access to medication storage of a use location and denied access to another location As shown in FIG. 11, a flowchart 1100 shows some of the steps performed automatically and can be performed without notification to an individual. The process begins with the checking in of the location 1102 of an individual. A determination is made in 1104 whether the individual is permitted to be at that location. If the individual is not permitted to be at that location, a response is triggered 1106. To help illustrate an example of geofencing, FIG. 12A shows an illustrative use location 1200. The use location 1200 may include a housing 1202 for the system as well as storage location 1204 that can be a building, area, or the like. The storage location 1204 may hold articles which can include manufacturing materials, medical devices, medicines, containers, instructions, manual, and the like. The use location 1200 may also include a task location 1206. The task location may be where tasks are performed using materials that can results in a medical device or medication.

Figure 12B:
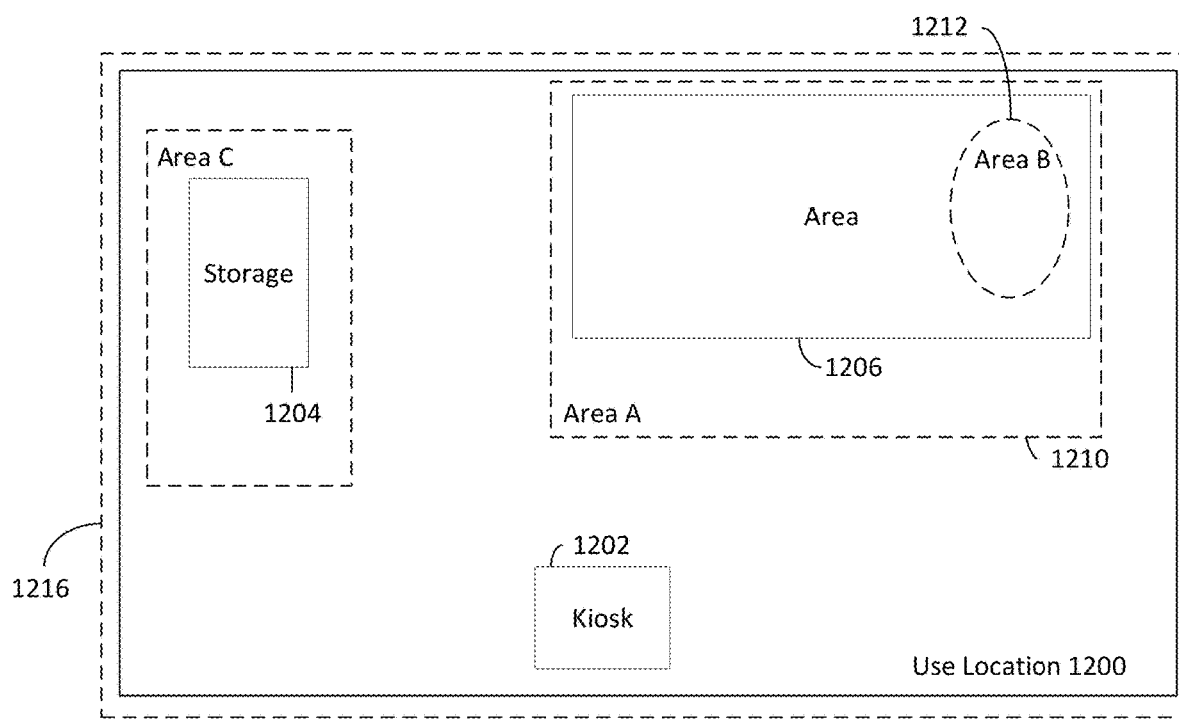
FIG. 12B shows a plan view with geofencing at a use location.

FIG. 12B shows an example of different areas that may be established for geofencing at the use location 1200. Area A shows a boundary 1210 may include the entirety of a certain use location 1206 (e.g., medication storage and research laboratory). Area B 1212 may be a portion of the use location, such as where article is stored. Area C 1214 may be another location and area D 1216 may be the entire use location. Individuals may have access to none of these areas, to a subset of these areas, or all areas.

When an individual enters an unauthorized area, an audio or video response can occur on the wearable. For example, a smart vest or other article may include lights that may flash or may be continuously illuminated in response to a party being outside the permitted areas on the use location. Another option is for an audio alarm or a video alarm to be triggered at the use location rather than on a wearable. A further option is to send a notification, such as a phone call, a text message, an email message, or other notification to a supervisor on or off the use location. Yet another option is to take disabling measures relative to the individual. The disabling measures could entail triggering locks or disabling equipment by shutting off power or the like. The geofencing can also be used to determine where the material will be delivered, stored, and installed. The geofencing, along with date and time information, can assist with the determination whether the material was handled or installed by a licensed, experienced, approved, authorized, or otherwise preferred individual.

Figure 13A:
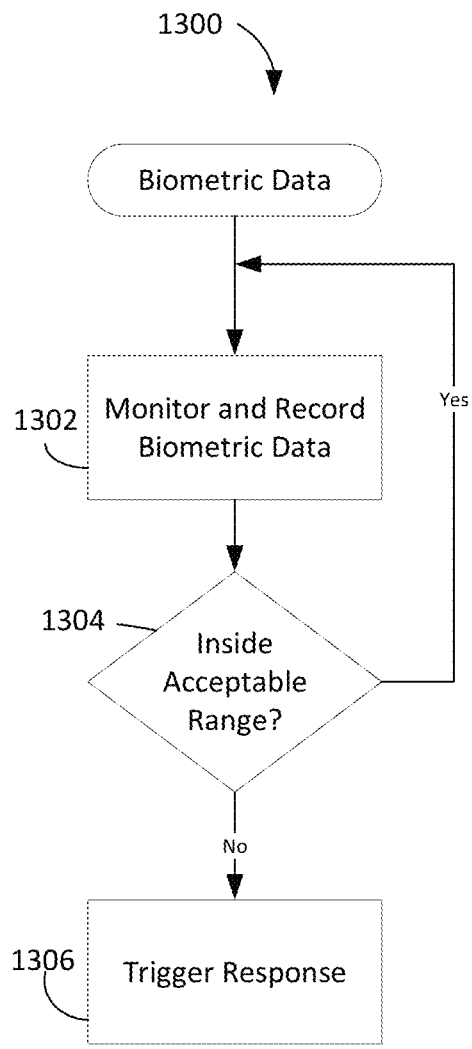
FIGS. 13A-13B show flowcharts is aspects of the system.
Figure 13B:
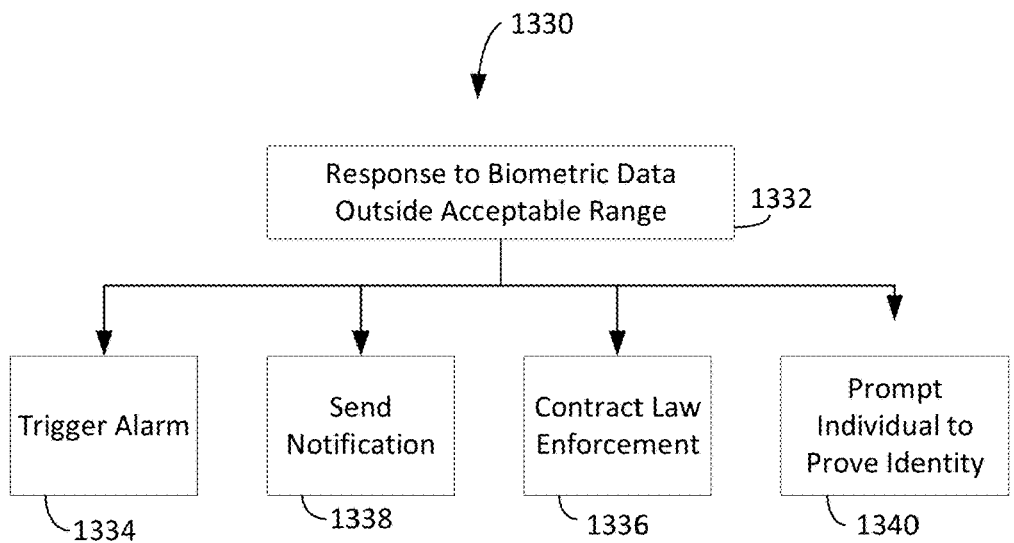

Referring to FIG. 13A, biometric data is capture and recorded as 1302. If the individual associated with the biometric data is not approved to be within an area at 1304, a response is triggered at 1306. Referring to FIG. 13B, if the biometric data shows that an individual is outside an acceptable range, an alarm can be triggered at 1332, notification of the alarm can be sent at 1338, law enforcement can be contacted at 1336 and the individual can be promoted to prove his identify at 1340.

Figure 14:
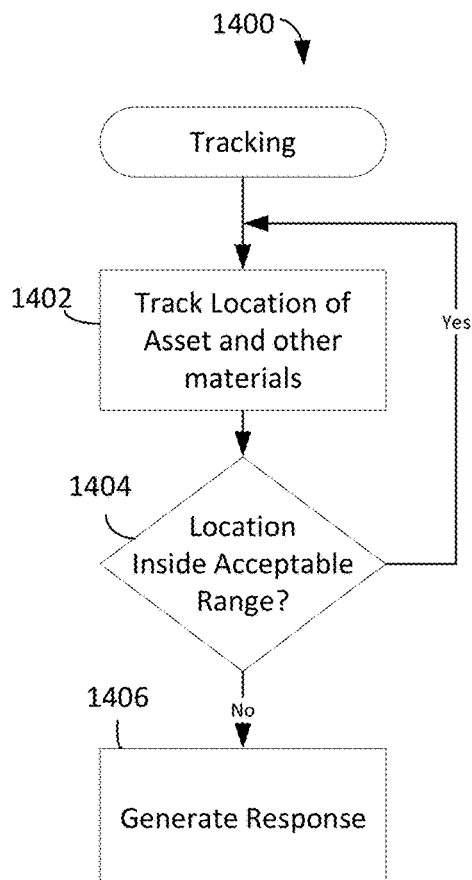

Referring to FIG. 14, the system may track the medical device, medication, or other article at the use location 1402. The system can check whether the location of the article. equipment, tools, or other materials is acceptable or not 1404. For example, suppose that raw materials have been delivered to the use location and the location of the raw materials indicates that the raw materials are removed from the use location. This would be problematic and would warrant a response. If the location is not acceptable as checked in 1404, a response is generated in 1406.

Figure 15:
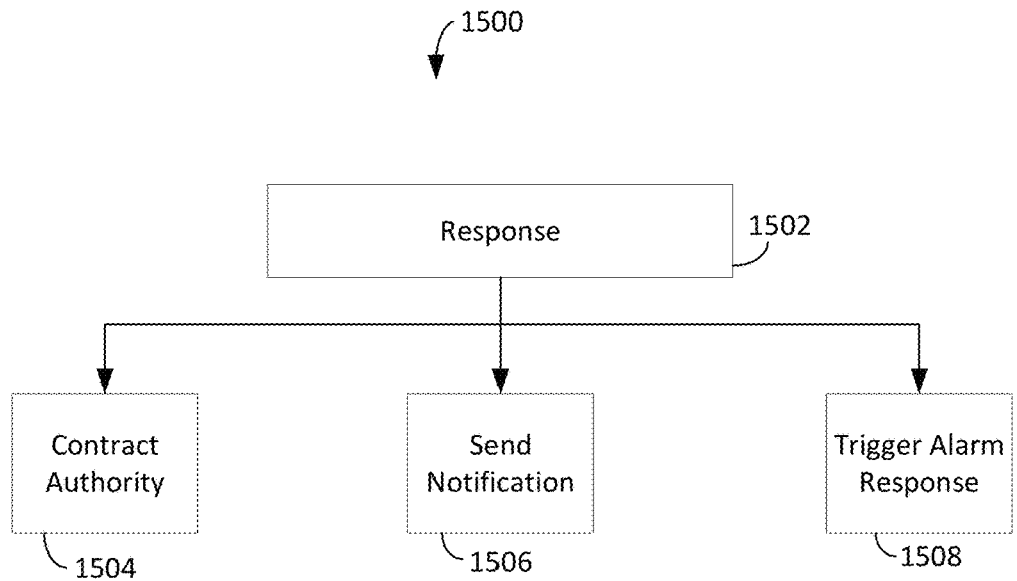

FIG. 15 shows a diagram 1500 illustrating different types of responses 1502 that may be generated in response to the article in an unacceptable location or an unauthorized access to the article location. One type of response is to contact law enforcement or security 1504. In many cases the article may indicate that a theft is underway. Another type of response is to send a notification to an individual or to other appropriate parties at the use location 1506. A final type of response is to trigger an alarm response 1508, such as the sounding of an audio alarm or a video alarm.

Figure 16:
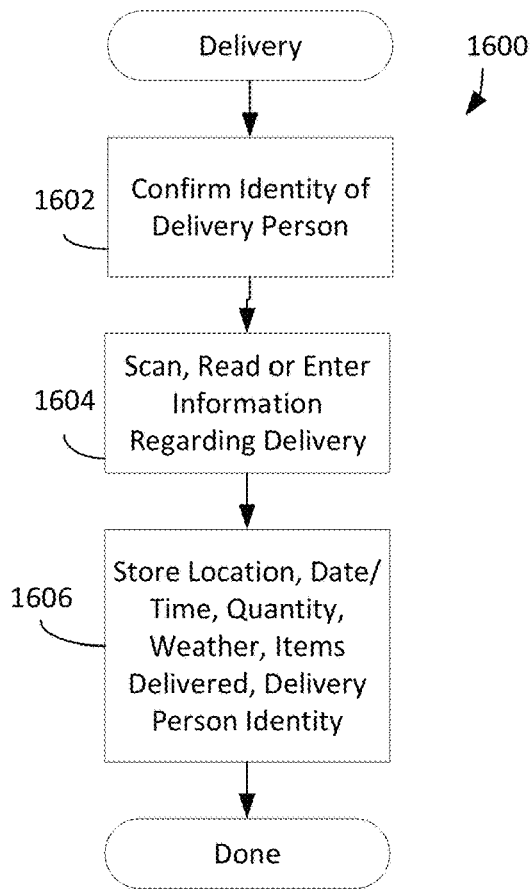

The system helps manage deliveries to and from a use location. FIG. 16 depicts a flowchart 1600 showing steps that may be performed regarding deliveries. Initially, the identity of the delivery person is confirmed to indicate that the delivery person is the appropriate party and is permitted access to the use location 1602. For example, a serial number or other identification indicator may be scanned or read from the delivered articles. In addition, information may be entered by the delivery person using the housing, such as by entering information via screen 106A (FIG. 1A) 1604. The location of delivery, the date of delivery, the time of the delivery, the quantity of the delivery, the identity of the delivery person and the environmental conditions may be recorded as part of the information that is kept regarding the delivery. This information can be used to track and confirm deliveries as well as to understand the conditions when the delivery was made.

Figure 17:
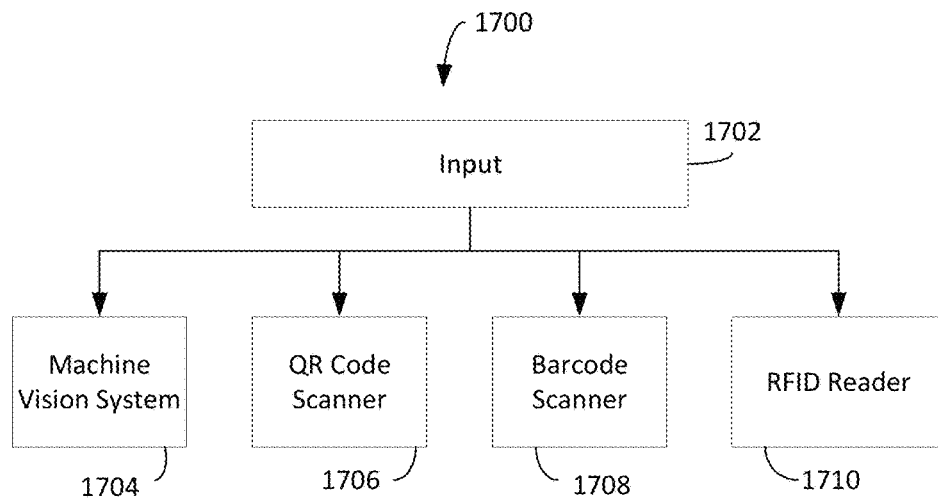

The deliveries may utilize various scanning and reader technology. In FIG. 1A, a scanner 110A may be provided. Diagram 1700 in FIG. 17 illustrates different types of inputs 1702 that may be used for assisting gathering information regarding deliveries. A machine vision system 1704 may be provided. The machine vision system 1704 may capture an image of the delivered items and process the image to determine the nature of the items that were delivered as well as the quantity of items. Moreover, the machine vision system may capture an archival image that may be indicative of the state of the items when they were delivered. A QR code scanner 1706 may be used where QR codes are on a delivered items or documentation. Similarly, a bar code scanner 1708 may be used where bar codes are on the items or on documentation delivered with the items. Still further, an RFID reader 1710 may be provided to gather information regarding the delivered items.

Figure 18:
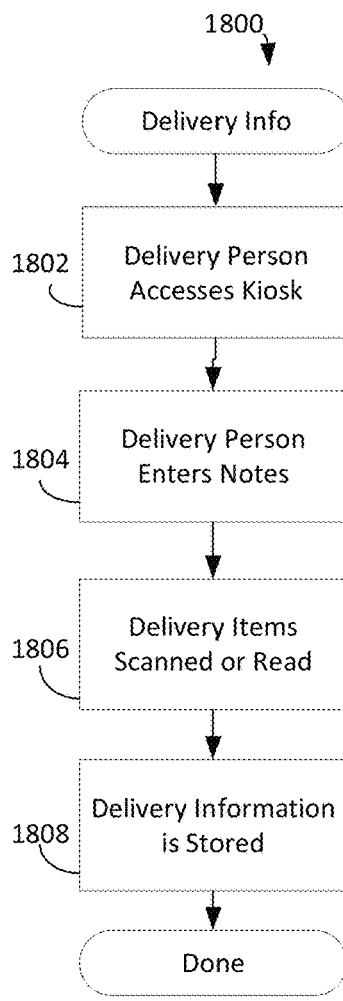

The delivery person may interface with housing via display 106A and 1900 to provide delivery information. Flowchart 1800 of FIG. 18 illustrates some of the steps that may be performed in such an instance. Initially, the delivery person may access the housing 1802. The delivery person may enter a note(s) regarding the delivery, such as what was delivered and the state of the items that were delivered 1804. This information may be entered, such as through the display 106A (FIG. 1A) which can be a touchscreen. The delivered items are imaged, scanned or read 1806. As was mentioned above, several different types of input technology may be used on the delivered items. Therefore, delivery information is then stored in records that may be accessed subsequently 1808.

When a transaction, other than an original entry of an article, a subsequent transaction, an individual (e.g., researcher, manufacturer, technician, custodian, certifier, inspector, and the like) may interface with the system. FIG. 19 includes a flowchart 1900 illustrating steps that may be performed in such an interaction. Initially, the identity of the individual, an inspector in this example, may be confirmed using the biometric data 1902 or manually using the touchscreen on the system. The inspector then performs the inspection of the article at the use location 1904. The inspector then accesses the system and provide information about the article we well as the system reading information about the article. The individual then may record notes and post certificates, notices, or other information at the system 1908. Additionally, the inspector may use technology available via the system such as OCR scanner, camera, or the like to capture appropriate information the individual may include during the recording of the article or transaction. If the system is at a drug trial, for example, the metadata about the trial activities, medications, medical devices, treatments, administrators, and subjects, can be recorded The system may include a still camera(s) or a video camera(s) that can be included in the system. FIG. 20 provides a flowchart 2000 relating to such access. A software interface to the camera may be provided to enable authorized external parties to gain access to the camera 2002. A party requests access to the camera via the interface over the network 2004. For example, a regulatory official may wish to view the use location before authorizing research and testing or before granting regulatory approval. A determination is made whether the party is permitted access by accessing permissions 2006. At least a portion of this information is persistently stored to compile a record of activities at the use location. This record can be useful to prove activities after the fact. The activities that are recorded may drive workflow and scheduling at the use location to improve efficiency. If the party is permitted access, access is given to the party so that they may receive a captured image or video data 2008. Otherwise, access to the camera by the party is denied 2010.

Figures 21, 22:
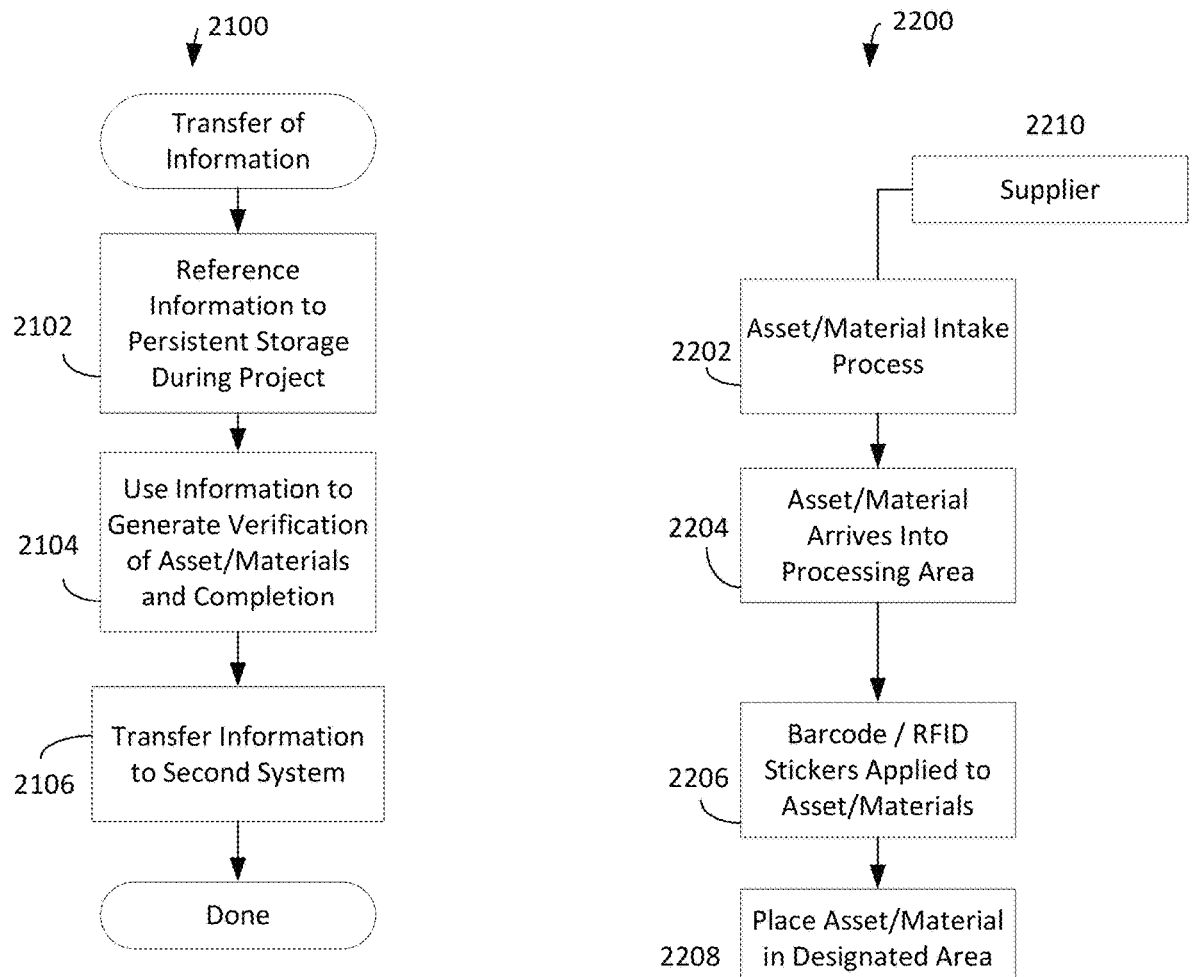

A great deal of information may be collected and stored during a project, process, or task for reference during authentication of transactions of an article. FIG. 21 shows a flowchart of steps 2100 that may be performed in exemplary embodiments in relation to the information. The information obtained about the article can be derived from many different sources may be stored on or referenced from persistent storage 2102. This information may help in the verifications, proof or other activity concerning authentication and validation of medical devices, tasks, medicines, research, results, and the like. Since there is a complete record including an audit trail on the persistent storage of all transaction, individuals, activities, tasks, locations, and the like associated with the article these records may be accessed to resolve any issues of authentication, verifications, results, and the like. Insurance providers may access these records referenced on the persistent storage to provide insurance or confirm claims. Inspection records may be accessed to confirm that proper inspections were carried out and passed. Various records may be accessed to confirm that proper processes, materials, tasks and the like were carried out and passed so that regulatory approval can be granted. A certification can be made a stored at 2104. The certificate of authenticity can be based upon the article and its transactions and stored on the persistent storage.

The record may hold information such as the article, design, materials, transportation, individuals, locations, warranties, confirmation of conditions, Payor information, insurance policy information, inspection history information, ownership history, history of localized events; like environmental conditions and records of trespassing (such as images), and bills of sale and receipts for articles.

The information referenced in the persistent storage may also be accessed from a computing device of a researcher, distributor, manufacturer, prescriber, user, dispenser, auditor, inspector, proposed buyer, insurance entity, creditor, customer, and the like at 2106. In exemplary embodiments, information may be gathered from and sent to multiple parties including a company responsible for the management and oversight of a medical device, medicine, or task.

The manufacturing company 2210 is responsible for the intake of materials specified in the material requirement record that are needed for a medica device or treatment. FIG. 22 shows a diagram 2200 of steps taken in the material intake process 2202. Materials arrive 2204 at a processing area of the supply company from the manufacturers and distributors. Items such as barcode stickers, QR code stickers, Bluetooth beacons, UHF stickers, micro dot, and RFID stickers are applied to the materials 2206 so that the materials may be identified and tracked. The materials with the stickers applied are placed in a designated area for packing 2208. The materials may then be packaged for shipment to the use location. A kiosk can capture and record data of this process.

Figure 23:
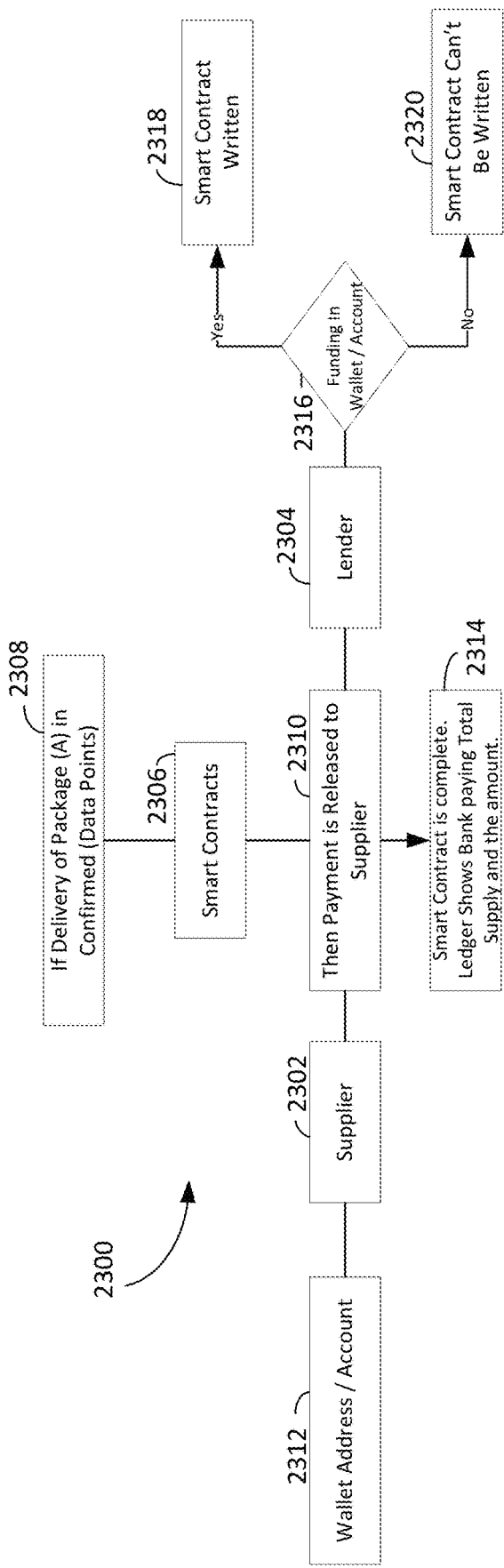
FIG. 23 shows different types of input technology.

FIG. 23 shows a diagram 2300 of a first example of interactions relating to a smart contract for the medical object including medical device, medicine, task, process, or project. Suppose that the supply company 2302 makes a delivery to the use location. Further suppose that the delivery is confirmed 2308 by information such as that gathered by the system as discussed above. The payor 2304 then releases payment 2310 to the supply company 2302. Payments can be made through third party funding, factoring, credit lines, loans, or other financial option to assist with financing and cash flow management. Payments can be effectuated with smart contracts when conditions of the smart contact are detected by the system. For example, when a healthcare worker provides a medical device or performs a treatment, uses medical equipment, or distributes medications, the system can record and store this activity and automatically submit a reimbursement request, such as to an insurance company.

The payment may be made electronically, such as through crypto currencies, like Bitcoin or Ethereum, fiat currency, electronic account, wallet, or stable coin whose value is pinned to an item as with paper currency or the like. A cryptocurrency is a digital currency built with cryptographic protocols that make transactions secure and difficult to forge. Other suitable forms of electronic payment include Automated Clearing House (ACH) payment, Electronic Funds Transfer (EFT), card payments, other types of bank transfers or other types of electronic wallet transfer. In the case where crypto-currency is used, the crypto-currency may be delivered to the digital wallet of the supply company at a specified wallet address or account 2312. The ledger may be updated to show that the contract is complete 2314. Payment requires that the Payor has sufficient funding in their digital wallet 2316. If not, the smart contract will not be written on the persistent storage 2320. If there is sufficient funding, payment is made, and the contract is written onto the persistence storage as complete at 2318.

Figure 24:
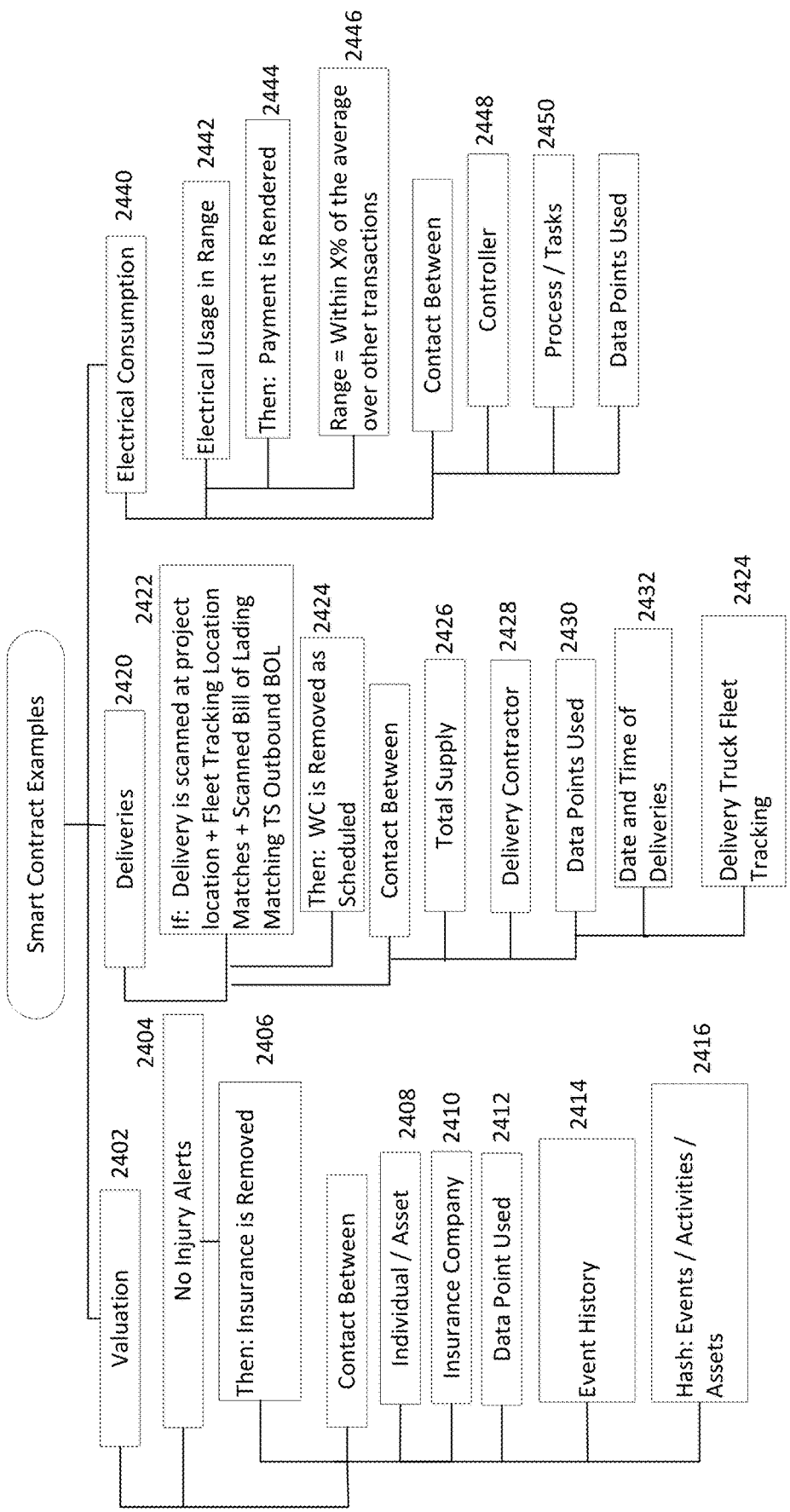
FIGS. 24-25 show flowcharts of steps that may be performed.

FIG. 24 depicts a diagram 2400 for multiple illustrative smart contracts. In a first illustrative smart contract, the smart contract concerns individual or article insurance 2402. The contract removes the insurance for an individual or article 2406 if there are no injury alerts for a given individual or article 2404. The smart contract can be between entities such as researchers, suppliers, sponsoring organization, manufacturers, buyer, users, sellers, etc. 2408 and an insurance company 2410. The contract looks at the data points 2412 of event history 2414 gathered by an identification item for the individual and any injury or other discrepancies reports 2416 from the individual. As mentioned above, the identification item may include a gyroscope or other mechanism that provides data indicative of a location change computer system an injury or other event which creates risk, causes damage, loss, medication use, the providing of medication treatment, job injuries, or the like. This data may be processed to identify data indicative of the event where an injury, loss or damage may have occurred.

A second illustrative smart contract shown in FIG. 24 relates to payment for a delivery 2420. If a scan is made at the delivery site, if the fleet location tracking information matches the desired delivery site location and if the scanned material list at the delivery site matches the outbound material list from the supply company 2422, then payment from the supply company 2426 to the delivery individual 2428 is made. Data 2430 used by this illustrative smart contract 2430 includes date and time of deliveries 2432 and delivery truck fleet tracking information 2424.

A third illustrative smart contract shown in FIG. 24 relates to electrical consumption 2440. By way of example, if the electrical usage by an individual, lab, manufacturing facility, or the like is within a range a certain percentage of the average use over a period of time 2442 and 2446, then payment is provided 2444 by the assembler 2450 to the system 2448. If not, the system can create and transmit a notification of the out of range use.

Figure 25:
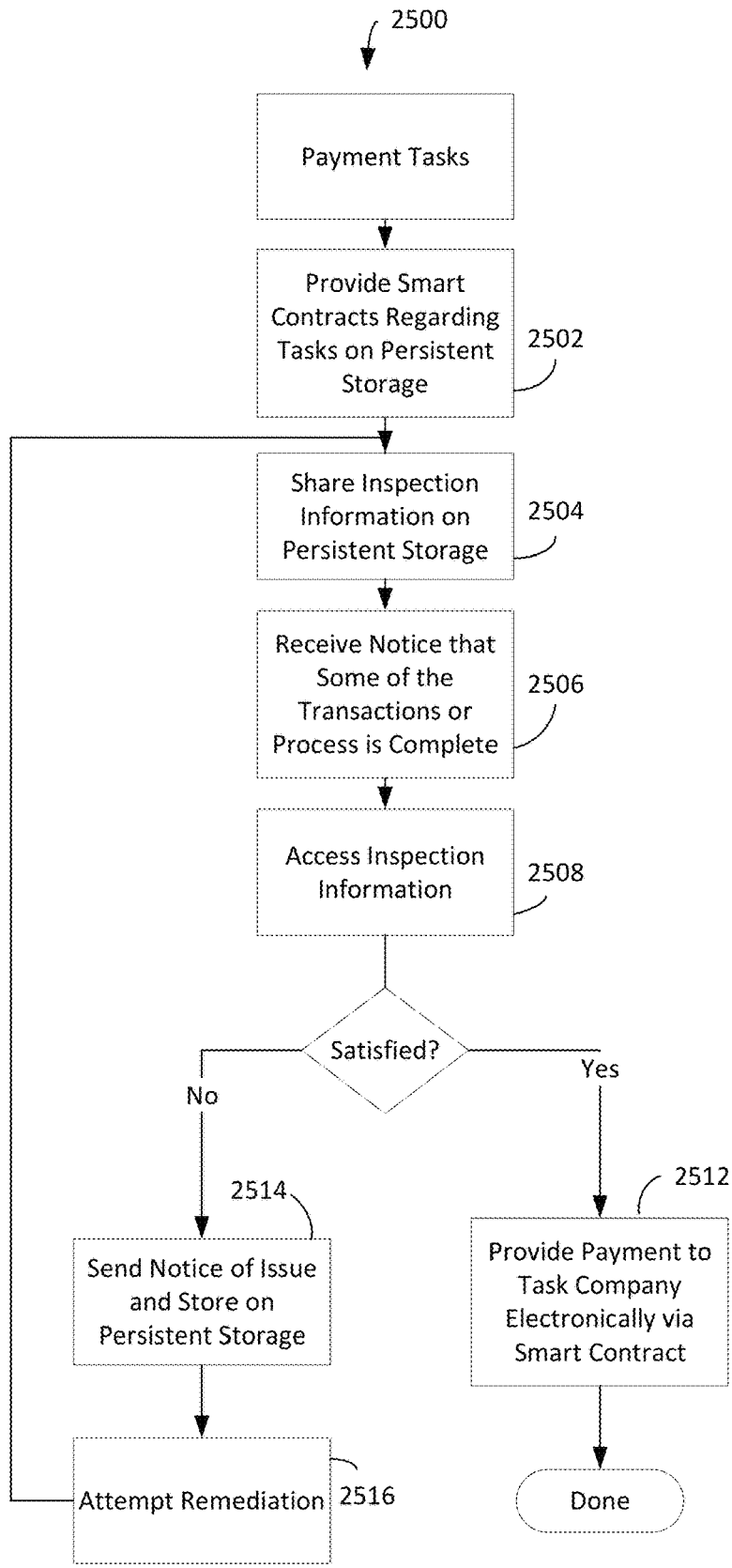

FIG. 25 shows a flowchart 2500 depicting steps performed for tasks of a project or process. Initially a smart contract may be initiated that uses the blockchain-based distributed ledger, where the smart contract is for at least a portion of the task for the project or process 2502. An inspection of work may be required or performed under the contract takes place and information regarding the inspection is passed through a hash function resulting in a hash value. The hash value may be referenced on the blockchain-based persistent storage 2504. The information may include, for example, the name of the inspector, the date of the inspection, an identification of what was inspected, an indication of whether the inspection was passed, any inspection notes from the inspector and an identification of any defects that cause a failed inspection and how to remedy. A notice is received at the system that a portion of the project is complete 2506. The inspection information is assessed 2508. If the inspection information indicates that the inspection was passed 2510, then payment may be provided 2512 to research lab, testing facility or manufacturing facility via smart contract. In contrast, if the inspection was unsuccessful, a notice of the failure and a notice of issues that need to be addressed may be sent, hashed, and resulting hash value may be referenced on the blockchain-based persistent storage 2514 for review. The lab, testing facility or manufacturer may then attempt to remediate the problems 2516 and repeat the above-described steps beginning with a new inspection and reference to a hash value for information regarding the new inspection on the persistent storage 2504.

To pair a medical device or medication with its virtual representation the system captures events at various points from raw materials to final distribution and use. Pairing the physical material with the virtual representation can include several elements or components. Included in the pairing process can be the physical observation of the materials to create a medical device or medication and its components and then associate the medical device or medication with a virtual representation so that the medical device or medication is properly associated with the virtual representation. This verification provides trust that the virtual representation is accurately associated with the medical device or medication as a fact rather than simply trusting that the virtual representation is accurate. This system can use manual or automated processes to physically observe the medical device or medication and its creation tasks and associate the medical device or medication with the virtual representation during various events from raw material to final deliverables. Verification can also use the metadata that is associated with the interaction of medical device or medication by individuals and electronics when the item is created, transported, installed, activated, and destroyed. The metadata that can be captured and placed into immutable storage can provide stakeholders an audit trail of history for their medical device or medication using a verified paired virtual representation. A similar process as described herein can be used for pairing a biometric identifier with an individual.

Verification, including verification of an event, can include verifying that the physical material and the virtual representation match and can be accomplished in a variation of methods including interaction with identification elements such as a tag, label, and the like, capturing an image of the material, capturing a video of the material, capturing a tag physically affixed or otherwise associated with the material, human visual inspection, and any combination. Identification of an individual performing or otherwise associated with an event can be captured by identification devices (e.g., cards, tags, RF ID) and biometrics including visual capture (e.g., facial recognition), voice recognition, iris scan, fingerprint, palm print and any combination.

Figure 26A:
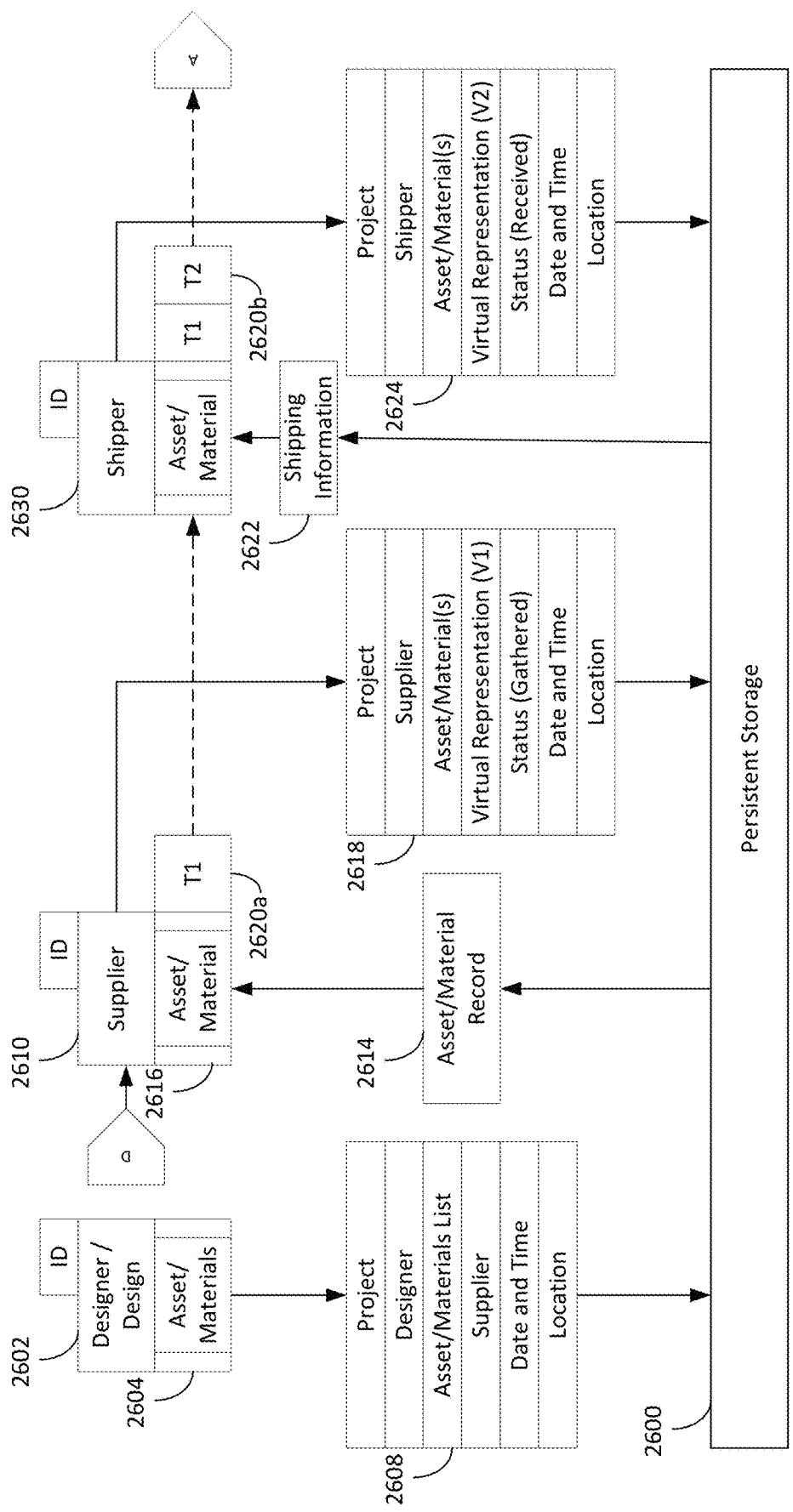
FIGS. 26A-26E shows schematics of aspects of the system.

Referring to FIG. 26A, an exemplary embodiment is shown. The persistent storage 2600 is accessible by a designer using a designer computer system 2602. The designer can have a unique ID associated with it. The designer can create an article design such as formulation, device, compound, medical device, and the like, that can ultimately result in a final medical device or medication. For example, the medical device can be a prosthetic, crutch, implant, and can be for general use or specific use. The medication can be any number of formulations. The design can include a material list and other properties for the medical device or medication. For example, if the article is an implant, the design can specify medical grade stainless steel, titanium, and other biomedical materials, tools, and equipment. There are a host of requirements that include multiple American Society for Testing and Materials standards. For example, if the medical device is for a knee replacement, ASTM F1223 provides for the material and test methods for the medical device. The system can create a designer record 2608 that can include information associated with the material, its manufacturer, is supplier, use location, supplier for one or more materials, the date and time the design was created or modified and the location where the design was created or modified and other metadata. The design record can be stored on the persistent storage that can be local or remote from the designer.

From the design record, a material record can be created and stored on the persistent storage. The material record can include a single component or multiple components. Each component or material in a set of materials can include a warranty that is from the researcher, tester, manufacturer, distributor, health care professional, installer, and any combination. The requirements for a warranty to remain in place can include requirements such as compliance with installation processes, environmental conditions, use of licensed individuals, use of qualified and experienced individuals and any combination.

Referring to FIG. 26A, a supplier, using a supplier computer system 2610, can select or otherwise acquire the material 2616 identified on the material list from a materials record 2618 or designer record that can be retrieved or otherwise received by the supplier computer system from the persistent storage. The supplier can verify that the material matches the material requirement record, and the system can capture this event. For example, one method of associating the physical material with a virtual representation is using a tag 2620$a$ ($T_1$) placed on the material. The tag is then physically verified to be associated with the material from the material list or the material record. Therefore, the physical material and the virtual representation ($V_1$) are paired by recording this event and associating the physical material, $T_1$, and $V_1$. The material can be received by the manufacturer, scanned, or otherwise identified with a sensor assembly, inspected by an individual and the manufacturing process recorded. This can include capturing the metadata associated with the material, individual, locations, date, time, and process as stated herein. In one embodiment, the tag can include the following information:

| Description | Digits | Information |
|---|---|---|
| Locations | 19-20 | GPS XX.XXXXXX XXX.XXXXXX |
| User ID | 8 | SSN XXXX + Initials XX + Gender X |
| Date | 10 | XX/XX/XXXX |
| Time | 7 | Zulu XXXX:XX |
| Material | 12 | UPC/Barcode XXXXXXXXXXXX |

A supplier record 2618 can be created and stored on the persistent storage. The capture event can include a unique number and include the supplier ID, date and time, location, material ID, status, and any combination. The material ID can be from an original manufacturer or the supplier. The status can include that the material has been gathered, manufactured, packaged, ordered, is in stock or on back order, shipping information and any combination. The supplier record can include or reference a designer or manufacturing specification record that can include the material and design requirements. The shipping information can include the origin, destination, shipping instructions, shipper, and any combination and can be included in or reference to the supplier record. The material be the medical device or medication.

Figure 26B:
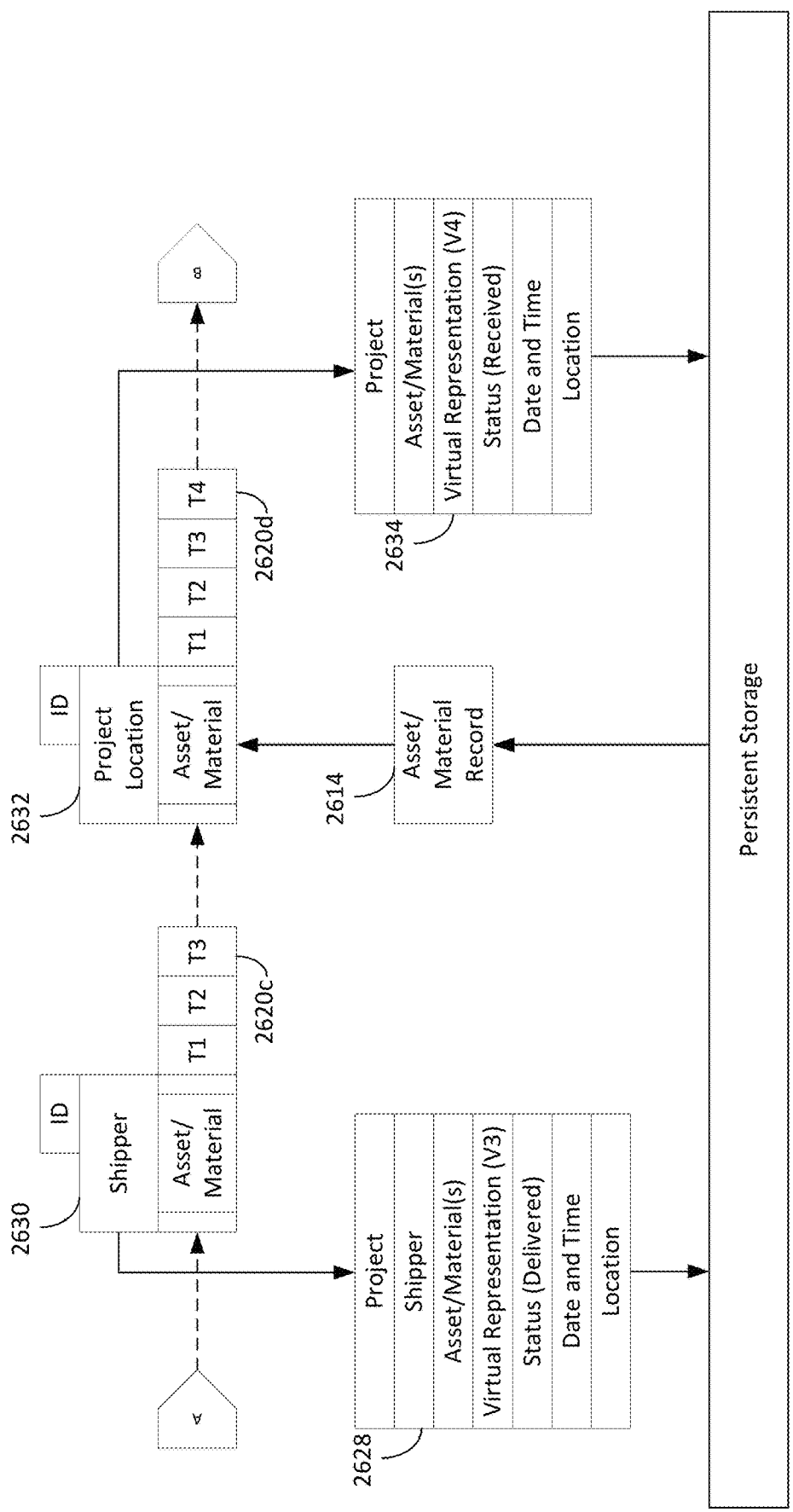

Referring to FIG. 26B, a shipper can retrieve shipping information from the persistent storage identifying the material, location, load, destination, pick time, delivery time, and other information concerning the shipping of the material or article. The shipper can verify that the material being retrieved from the supplier match the virtual representation of the supplier record. If the material is verified, the shipper can physically capture the event, for example, by affixing its tag 2620$c$ ($T_2$) to the material representing this verification. A supplier shipping pickup record 2634 can be created and stored on the persistent storage. The supplier shipping pickup record can include project, shipper, material, status, date, time, location, and any combination. The mode of transportation of the material can also be tracked and stored on the persistent storage. For example, if the shipper uses a vehicle, the date, time, location, and other metadata associated with the vehicle can be gathered along the route and stored on the persistent storage. Verification can be provided using the metadata of the various events associated with the material or article. For example, if the date, time, and location of the supplier record is within a certain range of values of the date, time and location of the supplier shipping pickup record, there will be verification that the proper materials were physically transmitted from the supplier to the shipper.

The shipper can deliver the material or article to the destination such as a use location. When the shipper delivers the material or article to the use location, the shipper can capture this event by creating a supplier shipping delivery 2628 record using a shipper computer system 2630. The shipper can verify the event by methods including adding a tag 2620$c$ ($T_3$) representing that the proper material or article was delivered to the proper location. The use location computer system 2632 can be used to verify that the material or article was properly delivered by retrieving the material record 2614 from the persistent storage and using the record to match the physical material or article delivered. In one embodiment, the shipper can use the tags that are part of the virtual representation to match $T_3$ with the material or article and the information stored on the persistent storage to capture and verify the event. When the material por article is delivered, the use location can use a computer system 2632 to retrieve the record from the persistent storage and match the material or article delivered with the material or article record. The use location can add a tag 2620$d$ ($T_4$) to the material to capture this event. The use location can create a use location received record 2634 that can include the project, material, article, virtual representation ($V_4$), status, date, time, location, other metadata, and any combination. The shipper, individual at the use location, or both can physically inspect the material and verify that it is matches the virtual representation stored on the persistent storage. This verification can be included in the information that is stored on the persistent storage by the shipper and an individual or system at the use location.

Figure 26C:
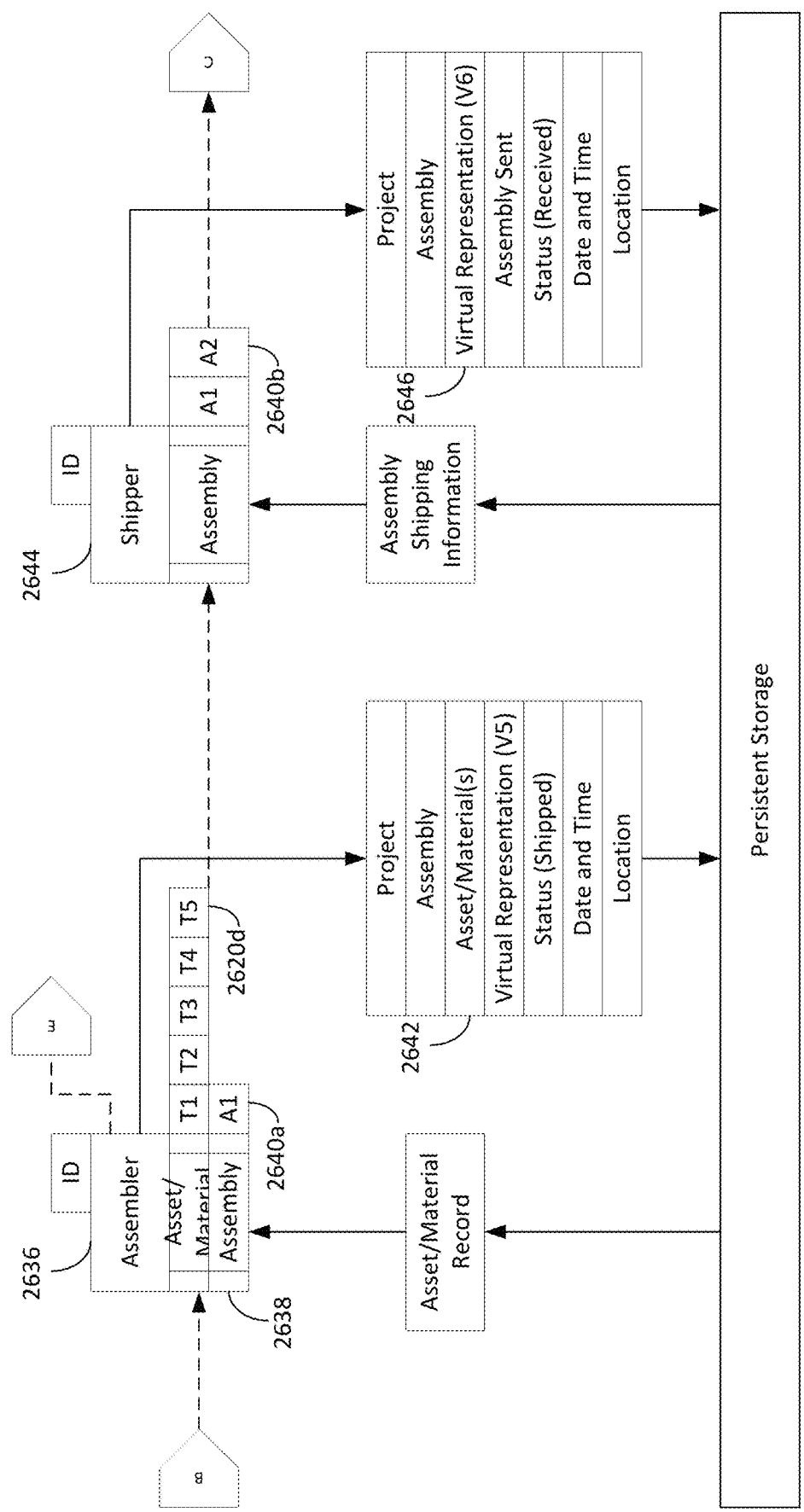

Referring to FIG. 26C, the use location can be a location that can manufacture, test, store, prescribe, fulfill, or distribute the medical device or medication. For example, if a medical device or medication has passed FDA approval, the system can verify the medical device or medication, add a unique identifier, record a pre-existing identifier, capture an image of the medical device or medication, and any combination and add the information into the system. The system can verify the information using the sensor assembly including capturing information about the medical device or medication or is components, individual, tasks, and the like. The unique identifier can be a number, bar code, alpha numeric characters, QR code, RFID, beacon, lot, size, sticker, tag, microdot, hologram, label, wireless transmitter, wireless transceiver, physical feature, and any combination. The physical feature can include a surface structure on the medical device or medication, a microstructure or other characteristics or manufacturing characteristics such as imprinting or tool marks. The unique identifier can include material identification added or associated with the medical device or medication record.

The system 2636 can be used to retrieve the medical device or medication record from the persistent storage. The medical device or medication record can be used to match the medical device or medication delivered to the use location to verify that the medical device or medication is properly associated with corresponding task, prescription, process, and the like. The use location can add tag 2620*d* ($T_5$) to the article, or use other verification methods described herein, to capture the event, task, medical device or medication. The system can also capture the medical device or medication and corresponding task at 2638 by adding a tag 2640*a* ($A_1$) to the medical device or medication. A medical device or medication record 2642 can be created, modified, stored or any combination on the persistent storage. The record can include the material, article, task, event, location, description, virtual representation, date, time, location, other metadata, and any combination.

Once completed, the medical device or medication can be delivered to another location such as through a sale of loan of the medical device or medication. The medical device or medication record can include shipping information, or an medical device or medication shipping record can be created and stored on the persistent record. If the medical device or medication needs to be delivered, a second shipper can use a second shipper computer system 2644 to retrieve the shipping record, medical device or medication record or other shipping information that is used to identify the origin, locations, article, pick up time, delivery time and other information associated with the transportation of the medical device or medication from one location to another and from one owner to another. The medical device or medication can be received by the second shipper and the second shipper can capture the event such as with a tag 2640*b* ($A_2$) to the medical device or medication record representing that the article has been verified by the second shipper as properly provided and received by the shipper. A second shipper pick up record 2646 can be created and stored on the persistent storage.

Figure 26D:
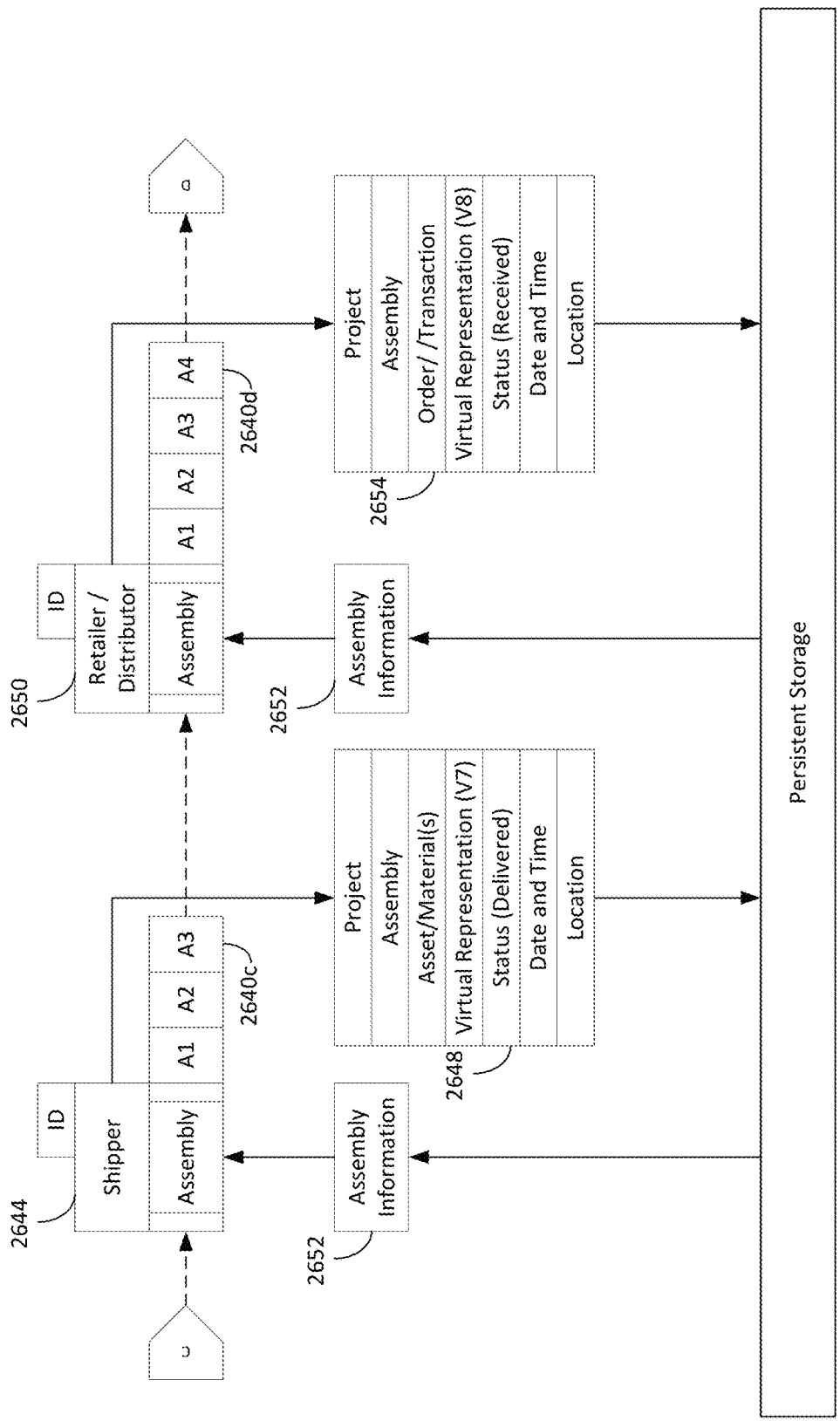

Referring to FIG. 26D, the second shipper can deliver the medical device or medication to a tester, regulatory authority, health care provider, prescriber, p[pharmacy, retailer, distributor, or patient. The medical device or medication can be transferred from an original owner to a subsequent owner. When the second shipper delivers the medical device or medication to a retailer or distributor, the second shipper can create a second shipper delivery record 2648 using a second shipper computer system 2644. The second shipper can capture the event such as using a tag 2640*c* ($A_3$) representing that the proper medical device or medication was delivered to the proper location. The second shipper can use the verifications that are part of the virtual representation to match $A_3$ with the medical device or medication and the information stored on the persistent storage.

The distributor or pharmacy computer system 2650 can be used to verify that the medical device or medication is properly delivered by retrieving the medical device or medication record 2652 or second shipper record 2648 from the persistent storage and using the record to match the medications or container delivered. The retailer or distributor can capture the event and can add a tag 2640*d* ($A_4$) representing that the proper medical device or medication was received at the proper location. A retailer distributor record 2654 can be created and stored on the persistent storage. Therefore, when a subsequent entity wants to verify the medical device or medication authenticity, the persistent storage includes the audit trail and chain of custody for the medical device or medication.

A healthcare provider may have ownership of the medical device or medication and therefore the right to transfer the medical device or medication to a second entity. The transaction can be recorded that can include the device ID of the kiosk, tag information of a tag associate with the medical device or medication, exchangeable image file data or other data associated with a photo of the medical device or medication, biometrics of the health care professional, certifier, seller, buyer, patient, pharmacist, or other individual associated with the medical device or medication, location and time certifications of certifier, buyer, and seller, wallet confirmation, medical device or medication number, hash confirmation, audit information, location over time for the medical device or medication and other information described herein. The system can also store medical device or medication and transactions associated with those in possession of the medical device or medication and those receiving possession and generate transaction history for the entities, jointly or separately that can include the data described herein.

Figure 26E:
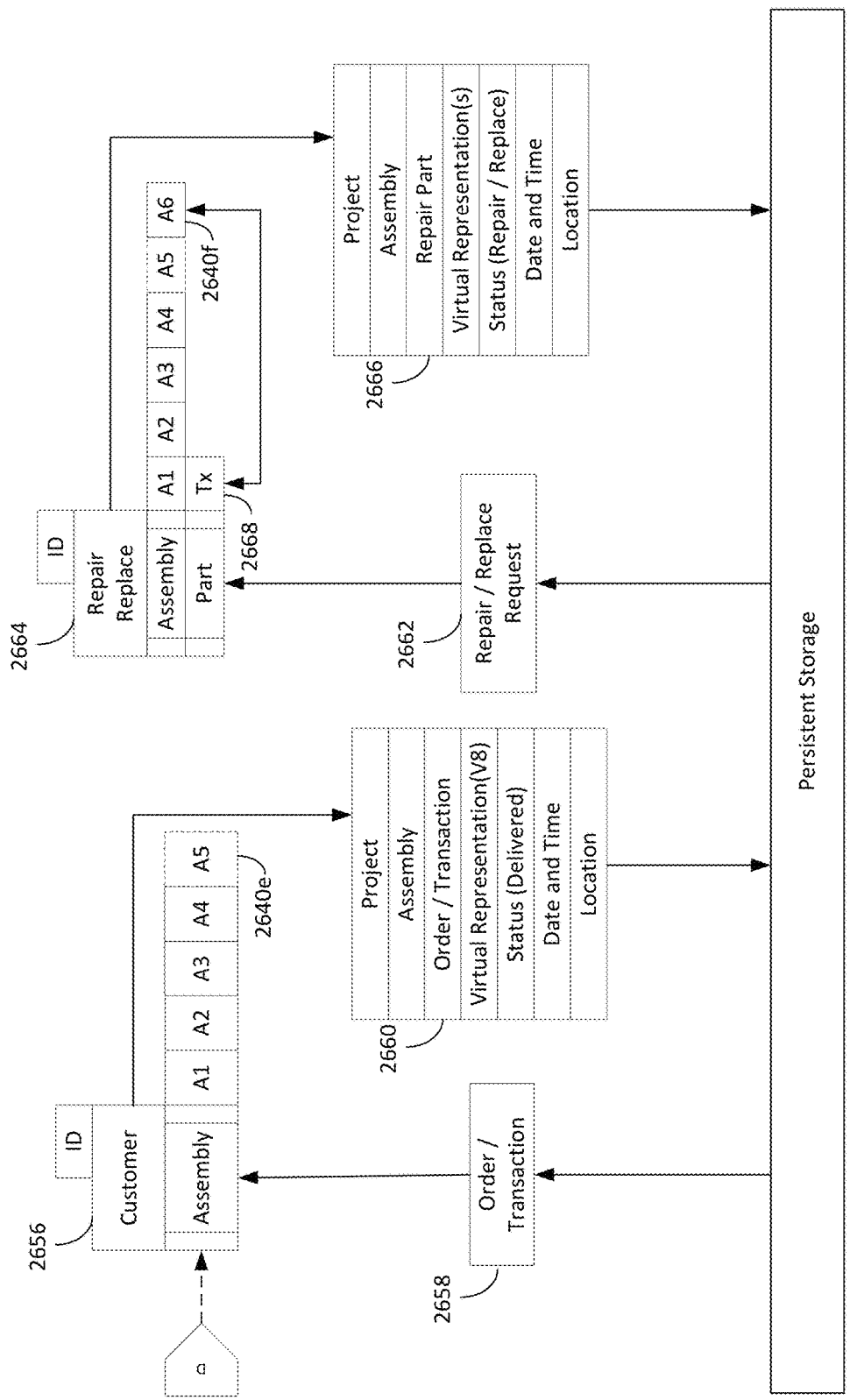

Referring to FIG. 26E, a buyer can receive the medical device or medication as using a computer system 2656 to retrieve or otherwise receive an order record 2658 from the persistent storage or other system requesting that a health care provider or patient receive the medical device or medication. The recipient of the medical device or medication can receive the medical device or medication using the system as described herein with a shipper performing the steps and the system performing the steps associated with the shipper and second shipper above. The recipient can receive the medical device or medication physically at a second location such as a medical facility. A third shipper can create a third shipper pickup and delivery record that can be stored on the persistent storage verifying that the medical device or medication was properly provided from the retailer or distributer to the next proper possessor. The possessor may capture the event and can add a tag 2640*e* ($A_5$) to the medical device or medication that can be associated with the virtual representation ($V_8$). A possession record 2660 can be stored on the persistent storage.

Using this system, the recipient or other entity can be assured that the medical device or medication was independently verified and authenticated from the design to the delivery to the recipient and that the virtual representation of the medical device or medication and its components (e.g., materials) are paired. Therefore, when purchasing a medical device or medication, the authenticity can be quickly and easily verified at the location of acquisition (e.g., medical facility or pharmacy) by accessing the persistent storage without the need for a third party or professional authentication process.

In one embodiment, a repair request 2662 can be created and stored on the persistent server. A repair may be required for a medical device. The repair request can be associated with the medical device and retrieved by a repair computer system 2664. The repair company can receive a medical device using the system described herein, perform a repair or replacement action, and capture the event such as by using a tag 2640f ($A_6$) to the medical device indicating that the medical device has had a repair. Any repair part can also have a preexisting tag from the use of the system herein and the repair company can capture the event such as by using a tag 2668 ($T_x$). A repair record 2666 can be created and stored on the persistent storage.

The system described herein can pair the medical device, medication, or container with a virtual representation. Failure to pair the medical device, medication, or container with the virtual representation can negatively impact areas such as authentication, certification, fraud prevention, health, legality, possession, abuse, and the like. Tracking, management, and verification of medical device, medication, or container to ensure authenticity and use and manufacturing is an important aspect to many medical device, medication, or containers. Tracking and record keeping during the life of a medical device, medication, or container from its creation to use can be difficult to perform without the ability to pair the medical device, medication, or container with ah virtual representation.

Systems at multiple locations may be interconnected using image capture devices, RFID, QR codes, barcodes, biometric scanners, still cameras, video cameras, and the like to identify individuals or machines that are performing verifications during the process. Further, multiple individuals or machines are performing verifications so that there is not a reliance upon any one entity for verifications. The processing of capturing data, including images, from the multiple systems at multiple locations can be used to improve the verification of proper materials and articles as well as to pair the physical items with the virtual representation.

This process can include internal and external individuals and machines for performing inspections (e.g., verifications). For example, the system can receive a set of internal inspection information entered into the system from an internal inspector representing an internal physical inspection of the project, material or assembly. As the items travel, an internal inspector can provide inspection information representing the stages of the project. The system can also receive a set of external inspection information from an external inspector and an external inspection computer device representing a third-party physical inspection of the project at predetermined stages of the project. Based upon the internal inspection, external inspection or both, an inspection record can be created and stored on the persistent storage.

Figure 27:
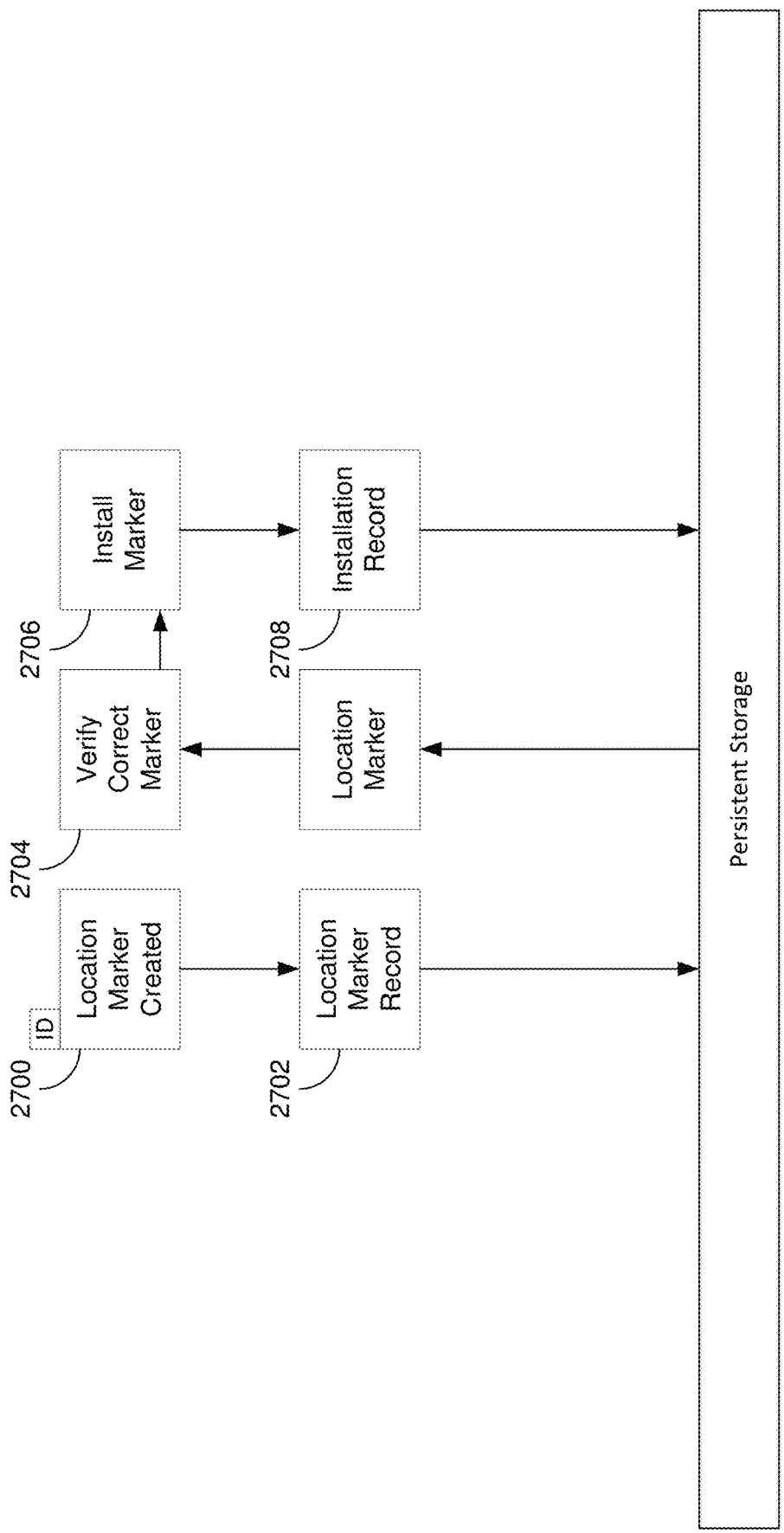
FIG. 27 shows schematics of aspects of the system.

Referring to FIG. 27, a location marker 2700 used to uniquely identify a location such as a use location and can include a research facility, testing facility, manufacturing facility, health care facility, pharmacy, retail location, distributor, wholesale location, warehouse, medical device, medication, or container location, or other physical location. The location marker can be a barcode, RF ID, placard, sign, plaque, QR code, or other symbolic, alphanumeric, digital, or electronic identifier. When creating the location marker, a location marker record 2702 can be created that includes the location marker identification information, creation date, maker, manufacturing location and other information that can be stored on the persistent storage. The installed information can retrieve the location marker record and match the retrieved information with the physical location marker to verify that the correct location marker is being installed at 2704. The installed can physically install the location marker and using a GPS enabled device, read the location marker, and create a location marker installation record 2708. The installation can be paired with the physical location marker and the physical location of the project. The metadata from the GPS enabled device can be included in a location marker installation record that can also include installer information, date, time, location marker information and physical location information and can be stored on the persistent storage. Therefore, the physical location marker is verified to be paired with the use location and a virtual representation of the location market and use location.

Figure 28:
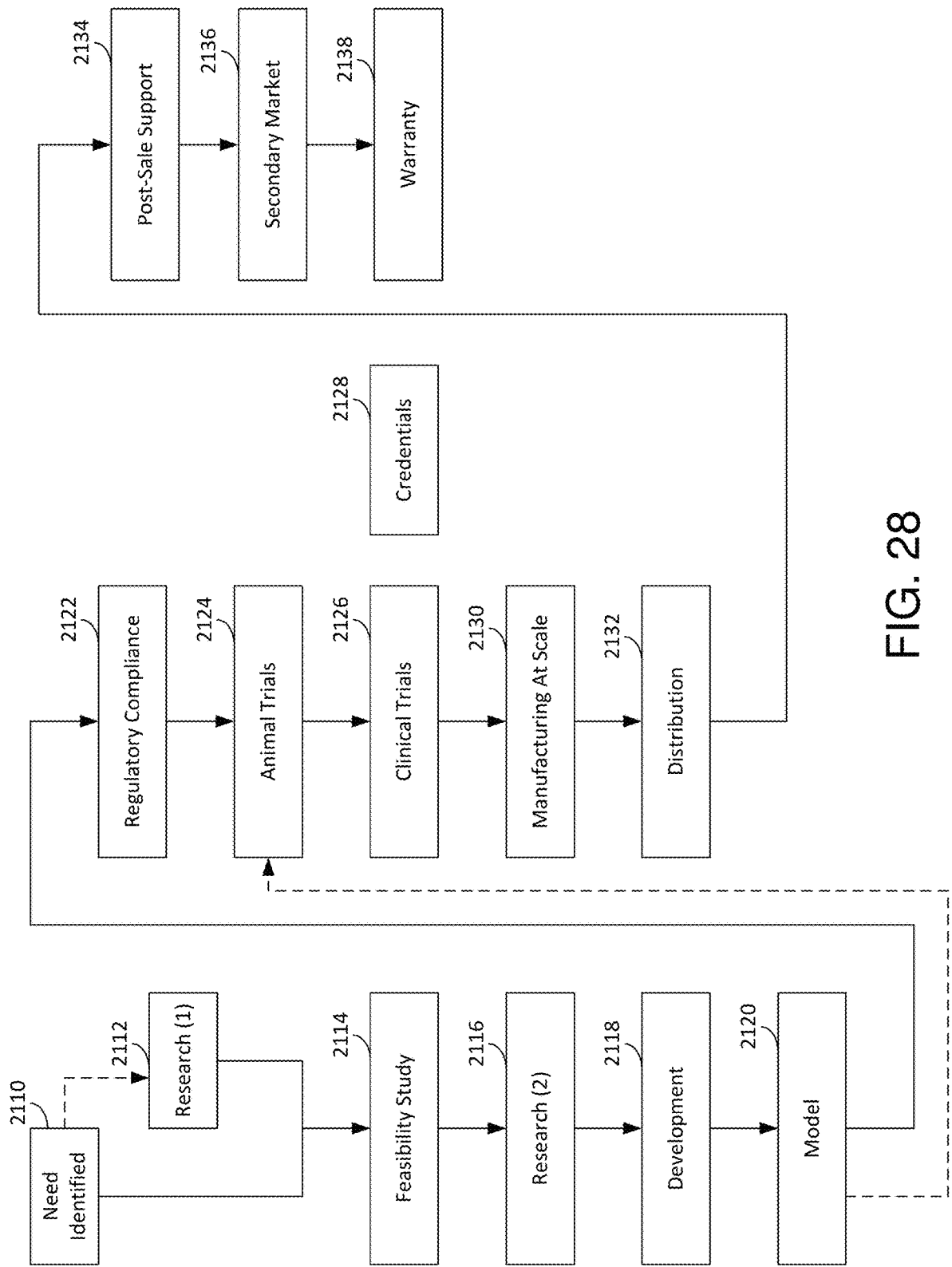
FIG. 28 shows a flowchart of aspects of the system.

Referring to FIG. 28, a need 2110 for a new medication or medical device can be determined or research 2112 can provide results that have the potential for addressing a mental or physical medical issues. Concerning the research 2112, the system can capture the materials used, individuals, tasks and other details of the research including the date, time and location and store the search record on the immutable ledger. Therefore, there is a virtual representation of the physical objects and the tasks associated and verifiable paired with the research. When a need is identified, research can be performed to determine if there is a medical device or medicine that can need the identified need. A feasibility study 2114 can be performed to produce several results including if the need can be satisfied, if the research satisfies the need, the cost benefit analysis, and other details. The system can capture the biometric information of the researcher, the materials used, the date, time and location and store the feasibility study record on the persistent storage. In one embodiment, additional research can be performed at 2116 that can include results directed to scalability, commercialization, target market, distribution, marketing, support, and the like that can be stored in a research record. The system can capture product development information 2118 that can include the individual, task, data, time, location, materials, and other information directed to the medical device or medication development. Materials can include raw materials, suppliers, costs, storage, processes (e.g., manufacturing, storage, shipping, delivery and use processes) and the like. A development record can be created and stored. The development can include a manufacturing process for the medical device or medicine. In one embodiment, at 2120, a model of the medical device or the medication can be made with in physical form of virtual. The model can be tested using computer aided design and modeling prior to the manufacturing of a physical product. This model can result in a model record being created and stored. In one embodiment, consideration for regulatory compliance 2122 occur as needed. For example, the Food and Drug Administration requires certain processes, investigations, test, and results prior to approving a medical device or medication for human use. These regulations include information about the investigator, prior human research, clinical protocols, manufacturing information, animal studies, trial design, and the like. The present system can include data capture, verified, and paired with a virtual representation for each of the stages herein.

The medical device, treatment, procedures, or medication could enter animal trials at 2124. The system can capture the materials, processes, date, time, and individual include the animals, dosages, dose, intervals, individuals, tests, results, and the like. The system can include a kiosk or computer system at the animal supplier that can track the generation, raising, shipping and receipt of the animal to the use location where the animal trial are conducted. The medical device or medication could enter clinical trials at 2126. The system can capture the materials, processes, date, time, subjects, researchers, use location and individual include the patient, dosages, dose, intervals, tests, results, and the like. The system can include a kiosk or computer system at the animal supplier that can track the behavior of the individual before, during and after the trial.

Are each stage of the process of a medical device or medicine, the individuals perform tasks can be recorded and stored. The licenses, permissions, and authorizations 2128 of the individual (including researchers, las technicians, etc.) can be capture using biometrics and associated with each material and activity. If an individual does not have the proper approvals, licenses, etc., the system can prevent the individual from accessing materials or locations as well as send alerts to third parties of the unauthorized attempt. For example, if a lab technician is not authorized to perform tasks for human trials, the individual can be prevented access to files, materials, medicines, medical devices, and the like.

Once the medical device is commercialized, either for profit or not-for profit, manufacturing can be made for scale at 2130. The system can capture the aspects of the manufacturing process including the individuals that are allowed to access a manufacturing location, areas of a manufacturing locations, the ordering of materials, receipt of the materials, processing of materials, providing a final product, shipping the final product and any combination. The system can also track the distribution of the medical device or medicine by recording and storing records for ordering, shipping receiving, delivering, as further described herein. The system can also track the tasks associated with post sale support including user assistance, repairs and replacements and the like at 2134. With certain medical devices, there can be a secondary market that can be supported by the system such as with medical devices like wheelchairs, crutches and the like, the subsequent transaction between the prior possessor and the subsequent possessor (e.g., a seller and a buyer) can be recorded with biometrics of the seller and buyer, date, time, location and medical device that can be stored in a transaction record that can assist with activities such as customer support, warranties, and the like. The system can also restrict a secondary market such as with controlled medications. The system can assist with the determination that a certain medication was previously dispensed to an individual and when compared with the biometric information of the possessing individual, the system can assist with the determination if the individual on possession of the medication is authorized. The system can demine if a medical device is under warranty at 2138 in a number of ways including retrieving use records, manufacturing records, storage records, shipping records, distribution records, transaction records and those otherwise described herein and determine if the medical device or medication is under warranty.

The images of FIG. 28 are presented in a linear fashion to explain the invention to those skilled in the art. One skilled in the art understands that the order in which these events occur or are arranged need not by in the illustrative linear fashion and at least some of the processes can be performed in parallel. The various records can be stored in the immutable ledger so that each record can be a block of a blockchain arrangement.

The system can be contained in one or more kiosks that are located at use locations such as labs, businesses, manufacturing locations, shipping locations, storage locations, dispensary locations, and the like. The kiosk can be in communications with each other or with the immutable ledger. One or more of the records described herein can be included in an audit trail associated with the medical device or medicine. The audit trail can be localized or disparate as the records that can be included in the audit trail can be localized or disparate.

Verification of an article of task can occur with direct information such as capturing the image of the article at a date, time, and locations, capturing the individual at a date, time, and location, capture a task, event or activity at a date, time and location and any combination. The data captured can be compared with external data such as occupancy information, access control information, shipping records, receipt records, and the like. When the captured data is compared with external data, discrepancies can be detected which can assist in the identification of issues such as fraud, mistakes, and the like. For example, when data about an individual is captured preforming a test, the system can correlate the date, time, and location of the test with an access system. If the individual accessed the location where the test occurs, the virtual representation that the individual is at that location can be verified. An image of individuals and article or task can be capture by the system and compared with third-party information such as occupancy, attendance, environment, and other information and if the third-party information is consistent with the transaction information, confidence in the authenticity of the truncation and article increases.

Third parties can use the system, such as an insurance company, certifier, authentication company and the like. The article record can be stored on the persistent storage so that the information cannot be subsequently tampered with. The article record can include a virtual representation of information associated with the medical device, medication, or container. In one embodiment, the article can be specified by class, type, product code, product number of other identifying information and virtual representation so that the material requirement record includes the article paired with the virtual representation which is verified by the certifier. This verification is independent of the other verifications described herein.

The article record can include manufacturing place, warehouse site, shipping information, transaction information or other information showing that the life of the article or task. For example, the article or task record can include the manufacturing location, serial number, date shipped, and date recited at a location. The article or task record can include when the article was used (e.g., in practice, during a game, etc.), the location where the article will be used, the location of the task and what the article or task will ultimately be used for.

When the medical device, medication, or container or component (e.g., article) is selected for transport by the manufacturer or supplier, a shipping company can be sent a shipping order representing the article to be transported. The shipping order can include the verifiably paired virtual representation and its information. The shipping company can be provided shipping information from the manufacturer, designer, supplier, or other company that can facilitate the transaction (e.g., broker, distributer, reseller). The shipping order can be provided directly to the shipping company or can be retrieved from the persistent storage. Once the shipping company receives the shipping order, it can travel to the desired article location and determine if the article in the shipping order match the medications or container at the desired location. A shipping pickup record can be created representing that the shipping company received the article and that the article picked matches the shipping order. This verification can be independent of the other verifications described herein.

Once that article is delivered to the desired location, the shipping company can unload the article and verify that the article that was unloaded was the same article included in the shipping order. The shipping company can create a shipping delivery record representing that the article was delivered and that the article matches the shipping order. The shipping record can include the environmental conditions when the article was delivered, delivery notes and the like. The shipping delivery record can be stored on the persistent storage. Receiving entity can review the article delivered and verify that the delivered article matches the design, article requirements, supply record, shipping order, shipping pickup record, shipping delivery record of any combination.

Once the article is received by the desired location, the system can notify individuals that the article is ready for distribution. The individuals can be verified by the system and an individual verification record can be created and stored on the persistent storage. The system can utilize biometrics or other systems as described herein for verification of actual individuals at the physical location to correspond with requirement for those that can verify that the article if authorized.

The system can identify individuals including when individuals are entering or leaving a location and store this information on the persistent storage. The information capture from the individual can through biometric identification devices such as a camera or other image capture device, facial recognition, voice recognition, retinal scans, fingerprint scanners, hand scanners, and other biometric devices. In one embodiment, the computing logic may allow authorized individuals to manually enter the presence of another authorized individual, including on the controller at the use location or through a remote device that can be determined to be at the use location, within a boundary associated with the use location, in proximity to the system. In one embodiment, individuals may be verified and paired with a virtual representation using two-factor authentication.

The individual can be provided with user information and specifications or other design requirements that can be represented by a task record. The task record can be stored on the persistent storage. Once installed the system can verify that the article was used (which can be individually inspected) according to the task record, create a task verification record and store the task verification record on the persistent storage. The task verification record represents that a task associated with the article was performed and can signify that the task was completed. The task record can represent that the task was performed by proper individual and in compliance with any requirements as well as if the article passes one or more inspections.

Prior to, during and after a task is completed, an inspection can be performed that can include a pre-task inspection, task inspection, post task inspection and any combination. A pre-task inspection, task inspection, and post task inspection record can be created so that the three records can be stored on the persistent storage. The task record can include information that the inspection resulted in passing, passing with deficiencies, and failing. If the inspection fails, the official, team, participants or players or other entities can be given the opportunity to remedy the failure and the inspection process can be performed again. The process can also determine if, while the task passed the inspection, the deficiencies should be remedied.

The system can be uniquely associated with the use location. A location marker can be affixed to the user location and uniquely identify the use location. The use location can be a research facility, lab, warehouse, shipper, distributor, storage area, health care provider, retail location, business, and the like. The location marker can be read by the system so that the system can determine its location. Third parties can read the location marker to determine the location. For example, the shipping company can arrive at the manufacturing location, read the location marker, and associate the location marker with the receipt and shipping of an article. In one embodiment, the manufacturer can receive a shipping identifier associated with the delivery, such as a truck, trailer, pallet, or other container so that the article is known to be received at the user location. Other parties can also access the location marker to verify that the third party is at the use location.

The system can be contained in a housing such as a kiosk and can be physically associated with the use location. The use location can be defined by a boundary representing the perimeter of the use location. The system can include a sensor and reader which can be selected from the group consisting of radio frequency identification (RFID) detector, ultra-high frequency (UHF) detector, a bar code scanner, a QR code scanner, near frequency communication (NFC) device; Bluetooth beacons, an optical character recognition (OCR) device and any combination thereof. An environmental sensor, such as a weather sensor or weather station, can be in communications with the or included in the housing and configured to record the weather and other environmental conditions at the use location and at different times during the project. This information can be used to verify the authenticity of the article.

The system may record the date and time of events such as the arrival and departure of materials and articles, individuals, technicians, health care workers, retail workers, officials, third parties, inspections, and the like to and from the use location, the date and time associated with environmental conditions including weather. Recording environmental information, including weather, at the use location allows for autonomous confirmation of environmental conditions that do not rely solely on third party sources or sources that are general or distant from the use location.

The system may also determine if an unidentified individual attempts to enter the use location, the system may take the appropriate responses, such as sending notifications, triggering alarms, and contacting law enforcement authorities or security. The decision as to the appropriate response may be determined by, the date, the time, current weather conditions, authorizations, project or process status, or related factors. This functionality of the system can prevent the loss of article such as a jersey, game ball or other article from being taken without authorization.

Figure 29:
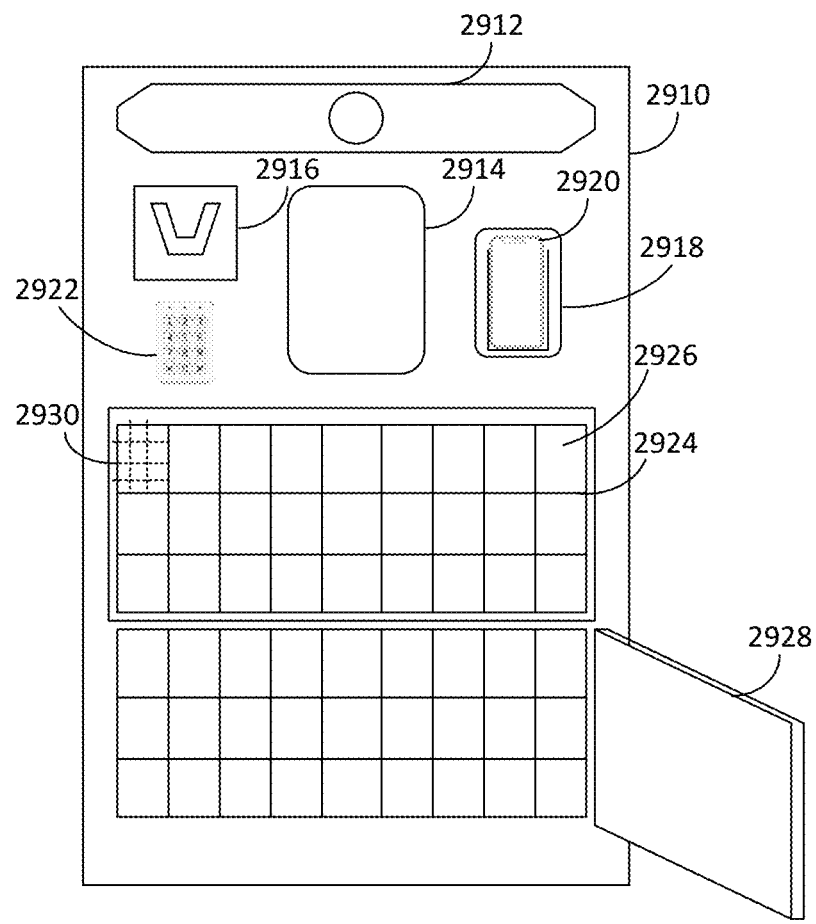
FIG. 29 shows a front view of aspects of the system.

Referring to FIG. 29, one embodiment of a dispensing kiosk is shown. The kiosk 2910 can include a sensor assembly 2912 that can include a camera, microphone, IR sensor, proximity sensor, near field sensor, optical sensor, the input devices described herein and any combination. The kiosk can include a display 2914 which can be touch screen and can be adapt4ed or configured for input including text, images, fingerprint, retinal and the like. A card reader 2916 can be included for receiving information from cards including card having magnetic stripe. The kiosk can include a cradle 2918 that can receive a portable computer device such as a smart phone 2920. The cradle can include a physical connection to the portable compute device or can include wireless connection. The portable computer device can include a camera, microphone, speaker and can be configured as an input device. The kiosk can include an alpha numeric keypad 2922 that can receive input. The housing can include one or more shelves 2924 that can hold medications. The shelves can include one or more openings 2926. When the kiosk approves access for an individual to retrieve a medication from the kiosk according to the information gathered by the kiosk, access can be granted such as by unlocking or opening door 2928. The openings can include security measures such a light beam 2930 that are projected across the opening by a light controller. The light beam can be one color indicating that access is not authorized and a second color indicating that access is allowed. If the light beam is crossed, and authorization is not allowed, alarms, notifications and other actions can be taken by the kiosk, including creating and storing an unauthorized access record and capturing data concerning the attempted access. The captured data can include images, date, time, opening, medication, and the like. The smart locks may also be used to limit access to certain portions of the use location, medical device, kiosk, or medications. An individual's right to a specific location may be dictated by permissions that are stored through each party involved in the process. This may eliminate keyed entry during the process and provide further verifications of individual or group access.

The sensor assembly and the kiosk can capture credentials of the individual seeking access to the kiosk (e.g., badges, licenses, etc.), biometrics, temperature inside and outside a housing, location (e.g., GPS coordinates), redundant power supply (e.g., chargers, solar panels), scanners, readers, wireless communications, and document scanner with OCR capabilities.

The individuals on the use location may be prompted to wear certain wearables that provide useful information to the system. For instance, individuals may be prompted to wear location tracking devices, such as GPS devices, Bluetooth, radio frequency identification (RFID) devices, ultra-high frequency (UHF) and beacon-based devices. The use of the wearables helps to perform geofencing within the use location. The location tracking provided by the wearable helps the system to monitor the location of individuals on the use location on an ongoing basis. The permissions may define what portions of the use location an individual may access. Ongoing monitoring may indicate that an individual is attempting to enter a location where the individual is not permitted. This may trigger a response as described herein. A signal may be sent to the vest or wearable to trigger a visual or audio cue that the individual is not in a permitted area. In addition, individuals may be requested to wear wearables that track biometric information, such as heart rate, body temperature, respiration rate and blood pressure. This information may be tracked and stored on an ongoing basis.

The system may track the movement of articles at the use location or to and from the use location. Scanning technology such as RFID readers, UHF readers and the like may be utilized to assist the location tracking of articles and even individuals. The tracking of article helps reduce the risk of loss, theft, mis-delivery, and the like. For example, the tracking solution may indicate instances of possible theft, such as when the article is leaving the use location when the removal of the article is not proper. Tracking can improve the confidence in the authentication of the article.

The system may allow for the establishment of one or more geofenced zone that can be associated with use location and location of the article. These locations can include entrance areas, exit areas, event areas, storage areas, and any combination thereof. These areas could be monitored and established with access allowances or restrictions to control movement of articles, individuals, and equipment to assist with the prevention of loss, mistakes, fraud, theft, inefficiencies, and damage. The system can assist with verification that article stored at these locations are consistent with the information concerning the article status, locations, state, etc.

The system, including a controller, may also interface with individuals to allow for the entry of notes and related details of a material, task, inspection, environmental condition individual, other task, process of individual or any combination thereof. For example, the system may allow an inspector to capture images of notes, forms, documents, labels, and the like using various readers, sensors, and input devices. The system can capture the use of the article such as during a game, on the sideline, etc.

Smart contracts may be provided that use the persistent storage for each event of the article is transferred the ownership and payment can execute upon satisfaction of terms of a transfer event. For example, when an article is delivered from a shipper to a use location and a verification of the article with is virtual representation occurs, this event can trigger a smart contact that instates payment to the shipper. When the article is transferred from one owner to another, the system can recognize the transfer, update the article record with new ownership, record the transaction, and automatically initiate payments or other funds transfer.

The system can be adapted to register a drug, medical device, or medical article or object at its point of origin which can include specifications and conformity issues not only for the transportation and handling of the article, that can assist with the integrity of manufacturing and transportation, but also that at the time of dosage, administration, or use a set of requirements related to that medical article. The system provides for confirmation of delivery to a set physical location (e.g., GPS identifiable location). The medical article is then registered to that location. At the time of an event, the system registers the location, date, time individual and articles using an immutable block chain or other persistent storage mechanism, registers the biometrics of the administrator or caregiver, as well as the biometrics of the person receiving the medical article. The system can immutably store this data associated with an asset record or other unique identifying record. These data points then can be used by the system to autonomously validate processes, payments, or progress points in an overall process. The system can include an auditing capability whereby when these data points are immutably recorded in the asset record, currently by a hash on an immutable block chain, the auditing functionality verifies the hash recorded in the asset record is recorded upon the referenced or corresponding block chain. The auditing component verifies the data recorded at the hash is the same data in the asset record results in a system that an identify anomalies and provide for predictive analysis.

What is claimed is:

1. A computerized system for verifiably pairing a medical object with a digital representation \comprising:
    a computer system disposed at a use location and in communication with a persistent storage;
    a medical object associated with a unique identifier;
    a set of non-transitory computer readable instructions included in the computer system adapted for:
        retrieving, from the persistent storage, a supplier record created by a supplier according to a first verification representing verification that a medical article is paired with a first virtual representation stored on the persistent storage, associating regulatory information with the unique identifier wherein the regulatory information is associated with the medical object and use location and wherein the regulatory information is taken from the group consisting of location, date, time, event, task, individuals, approval, and any combination, creating a medical object record having the unique identifier and according to the supplier record and the regulatory information, and, storing the medical object record in the persistent storage.

2. The system of claim 1 wherein the medical article is taken from the group consisting of a raw material, chemical, compound, medical device, medication, and medical container.

3. The system of claim 1 wherein the use location is taken from the group consisting of laboratory, testing facility, medical facility, healthcare provider facility, manufacturing facility, distribution facility, pharmacy, sales location, and any combination thereof.

4. The system of claim 1 wherein the medical object record includes a shipping information received by the computer system from a shipper computer system and the shipping information includes a second verification representing that the medical article received at the use location is the same medical article send by the supplier and received at the use location.

5. The system of claim 1 wherein the regulatory information includes biometric information of an individual inspecting the medical object during a regulatory approval process.

6. The system of claim 1 wherein the regulatory information includes biometric information of an individual inspecting the medical article.

7. The system of claim 1 wherein the set of non-transitory computer readable instructions are adapted to retrieve the medical object record, receive a recipient information, receive a distributor information, associate the virtual representation with a transaction according to the recipient information and the distributor information, create a transaction record according to the transaction, medical object record and a transaction verification information.

8. The system of claim 7 wherein the transaction verification information is taken from the group consisting of a biometric information of the recipient, biometric information of the distributor, recipient identification, verification of the distributor, verification of the medical article and any combination.

9. The system of claim 7 wherein transaction verification information includes an image taken of a medical article at a transaction location, transaction date, transaction time, transaction event, recipient, distributor, or any combination thereof.

10. The computerized system of claim 1 wherein the supplier record is created according to a physical verification of a first tag affixed to the medical article.

11. The computerized system of claim 1 wherein the supplier record is created according to a physical verification of a first tag affixed to a container adapted to receive the medical article.

12. A computerized system for pairing a medical article with a digital representation comprising:

a computer system disposed at a use location and in communications with a persistent storage;

a sensor in communications with the computer system;

a set of non-transitory computer readable instructions included in the computer system adapted for:

creating a medical article record using the sensor representing the medical article that is paired with a virtual representation wherein the virtual representation is included in the medical article record, creating a medical application record using the sensor having information taken from the group consisting of location, date, time, event, individuals, and any combination, associating a regulatory record with the virtual representation, and storing the medical article record and the associated regulatory record on the persistence storage.

13. The system of claim 12 wherein the medical article record and the associated regulatory record are configured to be retrieved from the persistent storage from a third-party computer system providing for verification that a medical article is authentic according to the medical article record and the associated regulatory record.

14. The computerized system of claim 12 wherein the computer system is contained in a kiosk.

15. A computerized system for verifiably pairing a medical object with a digital representation comprising:

a computer system disposed at a use location and in communication with a persistent storage;

a sensor assembly in communications with the computer system;

a medical object associated with a unique identifier;

a set of non-transitory computer readable instructions included in the computer system adapted for:

creating a medical object record using the sensor assembly representing the medical record that is paired with a virtual representation, storing the medical object record and the associated regulatory record on the persistence storage, receiving a medical individual information from the sensor, associating the medical individual information with the medical object record, and, storing the medical object record and the associated medical individual record on the persistence storage.

16. The system of claim 15 wherein the medical object record includes information taken from the group consisting of location, date, time, event, individuals, testing, compliance, and any combination.

17. The system of claim 15 wherein set of non-transitory computer readable instructions are adapted for receiving a transaction information associated with the medical object record, creating a transaction record according to the transaction information, receiving a smart contract criteria and implementing a smart contract according to the transaction record.

18. A computerized system for verifiably pairing a medical object with a digital representation comprising:

a computer system disposed at a manufacturing location and in communication with a persistent storage;

a sensor assembly in communications with the computer system;

a medical article associated with a unique identifier;

a set of non-transitory computer readable instructions included in the computer system adapted for:

creating a medical object record using the sensor assembly representing the medical object is paired with a virtual representation at a point of application, and storing the medical object record on the persistence storage.

19. A system of claim 18 wherein the set of non-transitory computer readable instruction are adapted for creating a transaction record representing a physical verification of a transfer of an article from a manufacturer to a second entity.

20. A system of claim 19 wherein the set of non-transitory computer readable instruction are adapted for transmitting a payment request according to a transaction record to a second entity account representing payment for the medical article from the second entity to the manufacturer.

21. A system of claim 18 wherein the medical object record includes manufacturing information verified to be associated with the medical article at a medical article creation.

22. The system of claim 18 wherein the set of non-transitory computer readable instruction are adapted for storing an individual verified record to the persistence storage adapted to provide conformity regarding a specification and a qualification of an individual associated with the medical object.

23. The system of claim 22 wherein the individual verified record includes data taken from the group consisting of vital signs, licenses, experience, training, authorization and any combination thereof.

24. The system of claim 18 wherein the set of non-transitory computer readable instruction are adapted for retrieving a medical article record from the persistent storage, retrieving a smart contact criteria, and transmitting an insurance claim medical article record to an insurance computer system according to a smart contract criteria.

25. The system of claim 18 wherein the medical object record includes a unique identifier associated with a recipient adapted for comparison with a payor and the set of non-transitory computer readable instruction are adapted for confirming a recipient's enrollment in a payor plan, determining that the medical object record is consistent with a payor criteria, and effectuating a payment to a medical provider.

26. The system of claim 18 wherein the set of non-transitory computer readable instruction are adapted for creating an immutable record representing a medical device wherein the immutable record includes location, time, biometrics of an individuals associated with a medical event, and verification of the medical device.

27. The system of claim 26 wherein the medical record is adapted for use by a participant, recipient, providers, facility, manufacturer, third-party stakeholders, and any combination thereof.

28. The system of claim 18 wherein the set of non-transitory computer readable instruction are adapted for creating an immutable record representing a medical activity wherein the immutable record includes location, time, biometrics of an individuals associated with the medical activity and verification of the medical activity.

29. The system of claim 18 wherein the medical record can be accessed by an entity taken from the group consisting of a receiver, payor, patient, test subject, participant, healthcare provider, insurance entity, and any combination thereof.

30. The system of claim 29 wherein the access is provided by use of a token.

* * * * *